(12) United States Patent
Barth

(10) Patent No.: US 7,867,782 B2
(45) Date of Patent: Jan. 11, 2011

(54) NANOSCALE MOIETY PLACEMENT METHODS

(75) Inventor: Phillip W. Barth, Portola Valley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 700 days.

(21) Appl. No.: 11/583,285

(22) Filed: Oct. 19, 2006

(65) Prior Publication Data

US 2008/0096287 A1    Apr. 24, 2008

(51) Int. Cl.
*G01N 33/543* (2006.01)
(52) U.S. Cl. .................... 436/518; 438/270; 438/258; 427/2.11

(58) Field of Classification Search .............. None
See application file for complete search history.

(56) References Cited

U.S. PATENT DOCUMENTS

2006/0134657 A1* 6/2006 Hodko et al. .............. 435/6
2007/0154881 A1* 7/2007 Koo ........................ 435/5
2009/0142472 A1* 6/2009 Barth et al. ............ 427/2.11

OTHER PUBLICATIONS

Choi et al., Delivery of catalytic metal species onto surfaces with dendrimer carriers for the synthesis of carbon nanotubes with narrow diameter distribution, 2002 J Phys Chem, 106 (48): pp. 12361-12365.*

* cited by examiner

*Primary Examiner*—N. C. Yang

(57) ABSTRACT

Methods and structures for placing nanoscale moieties on substrates are provided.

26 Claims, 11 Drawing Sheets

NANOSCALE MOIETY PLACEMENT METHODS

BACKGROUND

A general problem in nanotechnology is the siting of nanoscale moieties (nanomoieties) in sparsely packed deterministically located sites on a substrate surface. This difficulty arises because the sizes of nanomoieties such as nanotubes, nanowires, nanorods, nanofibers, quantum dots, and nanoscale seed particles (nanoseeds) can be on the order of 1-10 nm, smaller than the size of the smallest site that can be created at a predetermined location by an available method comprising one of scanning probe lithography, dip pen nanolithography, electron beam lithography, focused ion beam lithography, X-ray lithography, photolithography, and the like.

Several means have been developed to provide stochastically located, densely packed arrays of nanomoieties on a substrate, among which is the use of diblock copolymers. These means typically result in a structure with some local order, comprising for example a hexagonal close-packed array of nanomoieties on a planar surface, but the packing of the nanomoieties in arrays is dense rather than sparse and the location of an individual nanoscale moiety (nanomoiety) is random with respect to an overall coordinate system. Additionally, such means are incompatible with the use of pre-made photolithographic masks (photomasks) to fabricate additional features, either before or after, on the same substrate at predetermined locations with are far apart compared to the size of an individual nanomoiety.

One example of the need for a method of creating sparse arrays of deterministically located nanomoieties is the fabrication of integrated electronic circuits using carbon nanotubes. It is known that an individual nanoscale transistor can be fabricated on an insulating substrate by placing an individual instance of a carbon nanotube on the substrate, its length disposed parallel to the substrate surface, and then defining gate, source, and drain electrodes atop the nanotube and atop the substrate by lithographic means. However, the placement of hundreds, thousands, millions, or more of nanotubes on one substrate at sparsely packed deterministic sites consistent with fixed photomask patterns used for fabrication of many electrodes is problematic.

Another example of the need for a method of creating sparse arrays of deterministically located nanomoieties is the placement of elements comprising one of nanoseeds, quantum dots, nanotubes, nanorods, nanowires, nanofibers, and the like at well-controlled sparsely packed locations for purposes such as use in electron emitters. The placement of multiple such elements is often problematic.

Thus there exists a need for a method of placing multiple nanomoieties at locations on a substrate.

SUMMARY

Briefly described, nanomoiety placement methods and structures are provided. In an embodiment of a method of placing a nanomoiety at a deterministic location on a substrate, among other methods, the method includes: preparing a nanomoiety having a first characteristic dimension; providing as substrate having a surface; providing a nanoscale binding site at a deterministic location on the surface, the binding site having a binding patch, the binding site having a second characteristic dimension larger than the first characteristic dimension of the nanomoiety; associating the nanomoiety with a nanoscale delivery vehicle, the delivery vehicle having a third characteristic dimension larger than the first characteristic dimension of the nanomoiety, one of the nanoscale moiety and the nanoscale delivery vehicle having a binding region capable of binding at the binding patch; exposing the surface to a fluid delivery medium containing the nanomoiety associated with the delivery vehicle; stochastically contacting the binding region to the binding patch thereby binding the delivery vehicle to the substrate; and rendering the nanoscale moiety from the delivery vehicle to leave the nanoscale moiety attached to the substrate, the nanoscale moiety having a retention characteristic for continued attachment to the substrate after rendering. Other methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

Reference is now made to the following drawings. Note that the components in the drawings are not necessarily to scale.

DETAILED DESCRIPTION

Figure 1A:
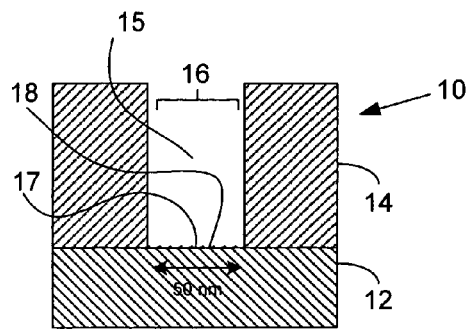
FIGS. 1A through 1K are cross-sectional views that illustrate a representative method of placing a nanomoiety on a substrate at a deterministically located binding site and employing the nanomoiety in fabricating a synthetic nanopore.

As will be described in greater detail here, nanomoiety placement methods and structures are provided. Advantageously, these methods allow nanomoieties (e.g., nanotubes, nanorods, nanowires, nanofibers, or nanoscale seed elements that can be used for growing nanomoieties (e.g., nanotubes, etc.)) having diameters on the order of about 1-10 nm to be placed at predefined large nanoscale binding sites on a substrate, wherein each binding site is substantially larger in a characteristic extent than the nanomoiety and is situated at a well-determined non-random location, but wherein the placement of each nanomoiety is achieved by employing stochastic (e.g., random) methods. Binding of the nanomoiety at the binding site may comprise one of, but is not limited to, Van der Waals attraction, hydrogen bonding, electrostatic charge stiction, ionic bonding, thiol bonding, and covalent bonding. The well-determined non-random location of the binding site is called a deterministic location. The methods of the present disclosure allow the accurate placement of a nanomoiety at a deterministically located binding site even though the binding site may be defined by a method such as electron beam lithography having resolution (e.g., about 50 nm) that is poorer than the resolution of definition for nanoscale entities such as nanotubes and nanowires, e.g. a diameter of several nanometers.

This advantageous characteristic, that is, the accurate placement of a nanomoiety having a first characteristic dimension at a deterministically located binding site having a second characteristic dimension which is larger than the first characteristic dimension of the nanomoiety, is achieved by associating (e.g., chemically, biologically, and/or physically) the nanomoiety to a delivery vehicle (e.g., as a payload to the delivery vehicle), the delivery vehicle having a third characteristic dimension large enough that only one delivery vehicle can occupy a given binding site. A given delivery vehicle is delivered to a given binding site by stochastic methods such as, but not limited to, thermal diffusion and chemical binding, thereby placing the associated nanomoiety at the binding site.

In one embodiment, the nanomoiety is then rendered from the delivery vehicle to leave the nanomoiety placed at the desired binding site. The nanomoiety has a retention characteristic so that it remains bound to the substrate after the rendering process. The retention characteristic may comprise one of, but is not limited to, Van der Waals attraction, hydrogen bonding, electrostatic charge stiction, ionic bonding, thiol bonding, and covalent bonding. The nanomoiety may be advantageously used in the fabrication of a useful device comprising one of a nanotube, nanopore, nanoscale transistor, integrated electronic circuit, integrated microfluidic circuit, ultrafast DNA sequencer, and the like.

The present disclosure includes methods and structures wherein a nanomoiety can be associated with a delivery vehicle which has a smaller third characteristic extent or dimension than the second characteristic extent or dimension of the binding site to which the nanomoiety is to be bound, and at the same time has a third characteristic extent or dimension greater than half the second characteristic extent or dimension of the binding site. These methods and structure include the use of a hole in a location layer, also known as a location and alignment layer. In these methods and structures the size of the delivery vehicle permits the delivery vehicle to enter the nanoscale hole but precludes more than one delivery vehicle at a time from binding at the binding site.

The present disclosure also includes methods and structures wherein a nanomoiety can be associated with a delivery vehicle which is larger in its third characteristic extent or dimension than the second characteristic extent or dimension of the binding site to which the nanomoiety is to be bound. In these methods and structures the large size of the delivery vehicle precludes more than one delivery vehicle at a time from binding to the binding site.

Embodiments of the present disclosure include methods of placing a nanomoiety at a pre-defined nanoscale site on a substrate, and are extensible to placing many such nanomoieties at many pre-defined sites on a substrate. The nanomoiety may be advantageously used in the fabrication of a useful device including one of a nanotube, nanopore, nanoscale transistor, electron emitter, integrated electronic circuit, integrated microfluidic circuit, ultrafast DNA sequencer, and the like. Arrays of nanomoieties may be placed on the substrate, and arrays of useful devices such as nanotubes, nanopores, nanoscale transistors, electron emitters, integrated electronic circuits, integrated microfluidic circuits, ultrafast DNA sequencers, and the like, may be fabricated.

Embodiments of the present disclosure include methods of fabricating arrays of nanomoieties in which the array packing is sparse, that is, the spacing between adjacent nanomoieties in the array is much greater than the dimensions of each nanomoiety so that, for example, an array of nanotubes, each nanotube having a diameter on the order of about 1 nm, may be placed in a rectangular array wherein adjacent nanotubes are about 50 µm apart.

Embodiments of the present disclosure include methods of fabricating arrays of nanomoieties in which the location of each element of the array is deterministic, that is, the location is pre-determined, equivalently pre-defined, by design with respect to one of the location of an adjacent nanomoiety and an overall coordinate system, to within the limits of accuracy of the method of creating the nanoscale site, so that, for example, a regular rectangular array of nanowires may be created wherein the location of each nanowire is pre-determinedly spaced about 50 µm±0.01 µm from an adjacent nanowire.

Embodiments of the present disclosure include methods of fabricating a nanoscale site by a method including one of electron beam lithography, optical lithography, X-ray lithography, UV lithography, deep UV lithography, scanning probe microscopy, dip pen nanolithography, stamp pad lithography, and the like. The location of the nanoscale site is determined by a design such as a design created by a computer aided layout tool, and the designed nanoscale site is fabricated by the method of fabricating the nanoscale site to the limits of accuracy of that method, and the location of the nanoscale site is said to be deterministic to within those limits of accuracy.

Embodiments of the present disclosure include methods of fabricating arrays of nanomoieties in which the properties of each nanomoiety in an array are well-controlled, and the distribution of properties among the various nanomoieties is tightly controlled. Advantageously, tight control of the properties among the various nanomoieties may be achieved prior to placement of the nanomoieties on the substrate by means comprising one of sieving, sorting, selection, purification, centrifugation, electrophoresis, separation, chromatography, binding, and the like which begin with a loose distribution of properties of nanomoieties and select for those nanomoieties having the desired properties. Properties of a nanomoiety may include one of dimensions, diameter, length, chirality, conductivity, semiconductivity, handedness, electrical charge, shape, and the like.

Embodiments of the present disclosure include methods of associating a nanomoiety to a nanoscale delivery vehicle having a binding region. The nanoscale delivery vehicle with its associated nanomoiety is placed in a delivery medium, comprising, for example, an aqueous solution. Other delivery media may comprise a gas, a dry powder, or a slurry. A substrate is prepared having a nanoscale binding site on a surface of the substrate. The substrate having the nanoscale binding site is exposed to the delivery medium containing the nanoscale delivery vehicle. Stochastic motion of the nanoscale delivery vehicle within the delivery medium, comprising for example one of: Brownian motion, convective flow, electrophoretically driven flow, ultrasonically driven flow, and the like, eventually places the nanoscale delivery vehicle in proximity to the nanoscale binding site in an orientation wherein the binding region of the delivery vehicle can interact with the binding site, while a third characteristic dimension of the delivery vehicle in relation to a second characteristic dimension of the binding site precludes other delivery vehicles from interacting with the binding site, and a binding event occurs wherein the delivery vehicle is bound in place at the binding site. A rendering event may then be induced, for example, by heating, to remove, react, oxidize, or reduce all or a portion of the delivery vehicle while leaving the nanomoiety bound to the nanoscale site. In an embodiment, the rendering process may comprise leaving the delivery vehicle in place. The nanomoiety after rendering has a retention characteristic that keeps it bound to the substrate at the binding site.

Embodiments of the present disclosure include methods of placing many nanomoieties in the delivery medium, each associated with one of many delivery vehicles, and many nanoscale binding sites may be formed on one substrate, allowing multiple nanomoieties to be bound to the substrate in one operation to form an array.

Embodiments of the present disclosure include methods of providing an excess of nanomoieties, including more nanomoieties than the available number of nanoscale binding sites on a substrate. The excess of nanomoieties may be placed in a delivery medium thereby increasing the probability that each nanoscale binding site will experience a binding event, and also thereby shortening the time required for most or all of the nanoscale binding sites to experience a binding event.

Embodiments of the present disclosure may be accomplished even when the minimum resolution of the means used to fabricate a binding site (described by a second characteristic dimension) is larger than the size of a nanomoiety (described by a first characteristic dimension) to be placed at the binding site.

According to embodiments of the present disclosure, a third characteristic dimension of a delivery vehicle may be larger than a first characteristic dimension of a nanomoiety and smaller than the second characteristic dimension of a binding site but larger than half the second characteristic dimension of a binding site, thereby establishing a situation where only one delivery vehicle at a time can occupy a given binding site. For example, the diameter of a cylindrical nanomoiety comprising a nanotube may be about 1 nm, the diameter of a circular pit comprising part of a binding site may be about 50 nm, and the diameter of a cylindrical proteinaceous delivery vehicle associated to the nanotube my be about 30 nm. In the situation of this example, only one such cylindrical proteinaceous delivery vehicle at a time can enter into the cylindrical pit because the cylindrical pit is too small to accommodate two such delivery vehicles simultaneously.

According to embodiments of the present disclosure, a third characteristic dimension of a delivery vehicle may be larger than a first characteristic dimension of a nanomoiety and larger than twice a second characteristic dimension of a binding site, thereby establishing a situation wherein only one delivery vehicle at a time can occupy a given binding site. For example, the diameter of a cylindrical nanomoiety comprising a nanotube may be about 1 nm, the diameter of an associated proteinaceous delivery vehicle may be about 50 nm, and the width of a binding stripe on a substrate to which the delivery vehicle is to bind along its long dimension may be about 20 nm. In this situation the presence of the delivery vehicle in a configuration bound to the binding stripe precludes other delivery vehicles from making contact with the binding stripe.

It will be appreciated that the binding of delivery vehicles to binding sites can be enhanced and optimized by many of the same considerations used in surface chemistry and fluid transport of many kinds. For example, in the hybridization of oligonucleotide strands in an aqueous solution to tethered oligonucleotide strands on a surface, process optimization depends on pH, temperature, salinity, fluid flow velocity, and time, among other considerations. Different types of binding processes require different types of optimization. Many different of binding mechanisms may be employed in embodiments of the present disclosure without departing from the spirit and scope of the disclosure.

In an embodiment, one of the nanomoiety and the delivery vehicle may include a reporter entity, the reporter entity including one of a fluorophore, a dye, a quantum dot, a radioactive particle, a molecular bar code, and the like. Such a reporter entity can provide one of in-process monitoring and post-process quality assurance of the success of placement of a nanomoiety at a binding site. Additionally such a reporter entity can provide data on fractional occupation of an array of binding sites at a time including one of during and after fabrication of an array of nanomoieties. The reporter entity may be removed from the nanomoiety during the process of rendering the nanomoiety from the delivery vehicle, or may remain associated with the nanomoiety after the nanomoiety is rendered from the delivery vehicle.

By way of an example, some embodiments provide for placing a nanoscale seed (nanoseed) particle, suitable for seeding later nanotube growth, at a deterministically located binding site by providing a location layer (also referred to as location and alignment layer) atop a substrate, the location layer being on the order of about 50-400 nm thick and having a binding patch (employing, e.g., a chemical binding mechanism, a biological binding mechanism, and/or a physical binding mechanism) at a binding site. For example, the binding site may include a binding patch situated on the substrate at the bottom of a nanochannel or pit about 50 nm in diameter and extending through the location layer. A delivery vehicle is disposed at the binding site by exposing the location layer and the substrate to a delivery medium comprising, for example, an appropriate liquid solution containing a plurality of delivery vehicles each associated with one of a plurality of nanomoieties.

The delivery vehicle may comprise for example, a ferritin protein molecule containing about 2000-4500 iron atoms plus additional associated protein structures to increase the diameter of the delivery vehicle to a range of, for example, about 30-45 nm so that only one delivery vehicle at a time can fit within a pit, 50 nm in diameter and extending through the location layer, to reach the binding patch at the bottom of the pit. Other delivery vehicle components may comprise oligonucleotides and/or poly(acrylic acid).

The delivery vehicle can have dimensions (e.g., a length aspect, a width aspect, and depth aspect, or equivalent dimensional aspects depending on the structure) different than described herein so that the dimensions cause only one delivery vehicle to fit within the pit and reach the binding patch.

The delivery vehicle also has a binding region for binding the delivery vehicle to the substrate at the binding site. For example, the substrate may include silicon dioxide, and a portion of the silicon dioxide may be exposed at the binding site. At the same time the delivery vehicle may have a binding region including an organosilane molecule, the silane component of the organosilane molecule having a binding affinity for the portion of silicon dioxide exposed at a binding patch of the binding site, and so having a binding characteristic for binding the binding region having the organosilane molecule to the substrate at the binding site. In another embodiment, a binding patch at the binding site may be occupied by a layer of oligonucleotides tethered to the substrate by an organosilane layer, and the delivery vehicle may be covered with oligonucleotides complementary to those tethered on the substrate in the binding patch, the oligonucleotides on the delivery vehicle having a binding affinity for the complementary oligonucleotides occupying the binding patch and so having a binding characteristic for binding the delivery vehicle to the substrate at the binding site. In this embodiment the binding region may cover the entire surface of the delivery vehicle.

The location layer may include, but is not limited to, an electron beam resist having a low non-specific binding affinity for the binding region of the delivery vehicle.

The delivery medium may include, for example, water containing a plurality of delivery vehicles. Once the delivery vehicle is in place at the binding site, the delivery medium is removed. The location layer may be removed, for example, by washing in a solvent, advantageously removing any delivery vehicles that have undesirably bound to the location layer surface by nonspecific binding.

In one embodiment, once the delivery vehicle (e.g., including iron atoms in a bioferritin molecule) is bound to the binding site, the substrate may be heated in oxygen, oxidizing everything on the substrate surface so that the nanomoiety payload comprising an iron oxide seed particle, for example, is rendered from the delivery vehicle by the process of oxidation and remains in place at the binding site, while carbon, hydrogen, nitrogen, and sulfur atoms present in the delivery vehicle are removed. The nanomoiety may subsequently form the seed element for growth of a mandrel nanostructure useful in fabricating a nanopore for DNA sequencing, as described in patent application (patent application Ser. No. 11/487,550, filed on Jul. 14, 2006), which is hereby incorporated herein in its entirety by reference.

Advantageously in this example, the delivery vehicle may include a reporter entity (e.g., a fluorophore, a dye molecule, a quantum dot, or a radioactive particle) to indicate successful disposition of the nanomoiety at the location site, thus providing in-process quality assurance data.

Many deterministically located binding sites may be present on the surface of a substrate, enabling the formation of well-ordered arrays of nanomoieties on the surface of the substrate, and such arrays may be used for a variety of purposes. Variations on the methods of this example are suitable for building arrays of nanoscale transistors. Additional variations and uses of the methods of this example will occur to those skilled in the art.

Further, multiple nanomoieties to be delivered to multiple binding sites may advantageously have a tight distribution of size achieved through a process comprising one of sorting, sieving, separating, purifying, and the like of the nanomoieties prior to introducing the nanomoieties in the delivery medium to the binding sites.

By way of another example, some embodiments provide for placing a nanomoiety (e.g., a carbon nanotube) at a deterministically located binding site, the binding site having an orienting characteristic (e.g., dimensional aspects or chemical, biological, and/or physical features that cause a certain orientation) by providing a location layer atop a substrate, the location layer being on the order of about 50-400 nm thick and having a binding site. For example, the binding site may include a nanochannel or nanopit of about 50 nm in diameter, the nanochannel or nanopit having near-vertical walls and extending through the location layer to a binding patch on the substrate having a binding characteristic.

Next a delivery vehicle having an orientable characteristic (e.g., dimensional aspects or chemical, biological, and/or physical features that cause a certain orientation) is placed at the binding site by exposing the location layer and the substrate to a delivery medium. The delivery medium includes a liquid solution containing a plurality of delivery vehicles, each such delivery vehicle being associated (e.g., chemically associated, biologically associated, and/or physically associated) to a nanomoiety. The delivery vehicle may include, but is not limited to, a protein-based nanorod coupled to a nanotube using methods as discussed in "Non-covalent Sidewall Functionalization of Single-walled Carbon Nanotubes for Protein Immobilization," R. Chen, Y. Zhang, D. Wang, and H. Dai, *J. Am. Chem. Soc.*, 123 (16), 3838-3839 (2001), which is incorporated herein by reference, and surrounding the nanotube.

The nanorod may have a third characteristic dimension comprising a diameter of, for example, about 30-45 nm so that only one delivery vehicle can fit within a pit having a second characteristic dimension of about 50 nm in diameter and bind to the substrate, while the presence of the delivery vehicle precludes other delivery vehicles from entering the pit and reaching the binding patch. The delivery vehicle also has a binding region for binding the delivery vehicle to the substrate at the binding patch. One or both ends of the delivery vehicle may include a binding region, or the binding region may cover the entire surface of the delivery vehicle if non-specific binding with the walls of the nanochannel is small.

For example, the substrate may include silicon, the binding patch at the binding site may be occupied by a layer of antibodies coupled to the substrate by an organosilane layer, the nanomoiety to be delivered may be a carbon nanotube having an iron seed particle remaining at one end after prior growth of the nanotube, and a binding region at one end the delivery vehicle nearest the iron seed particle may be decorated with antigens specific to the antibodies in the binding patch.

The location layer may include an electron beam resist with a low non-specific binding affinity for the antigens in the binding region. The delivery medium may be water, for example, containing a plurality of delivery vehicles. Thermal diffusion of the delivery vehicle in the delivery medium results in the antigen-decorated binding region of the delivery vehicle binding to the antibodies at the binding patch. Once the delivery vehicle is bound in place at the binding site the delivery medium is removed and any remaining unbound delivery vehicles are washed away.

In one embodiment, the location layer may be removed, for example, by washing in a solvent, advantageously removing any delivery vehicles that have undesirably bound to the location layer surface by nonspecific binding. The substrate may then be heated in a reducing atmosphere, for example, serving to cause iron-to-silicon bonds to occur at the region where the nanotube adjoins the silicon substrate and serving to volatilize organic compounds present that do not exhibit the strong carbon-to-carbon bonds of the nanotube. The iron-to-silicon bonds then comprise a retention characteristic to the substrate for the nanomoiety comprising the nanotube payload, keeping the nanomoiety bound to the substrate. The carbon nanotube may subsequently form a mandrel useful in fabricating a nanopore for DNA sequencing, as described in patent application (patent application Ser. No. 11/487,550, filed on Jul. 14, 2006, which is incorporated herein by reference).

Advantageously in this example, the delivery vehicle may include a reporter element (e.g., a fluorophore or a quantum dot or radioactive particle) to indicate successful disposition of the nanomoiety at the binding site.

Many binding sites may be present on the surface of a substrate at deterministic locations, enabling the formation of well-ordered arrays of oriented nanomoieties (e.g., nanoscale mandrels or nanotubes, nanorods, nanowires, or nanofibers), each nanomoiety being located at one of the deterministic locations, and wherein the density of the array is controlled and determined by the deterministic placement of the binding sites.

Further, the oriented nanomoieties may advantageously have a tight distribution of properties achieved through a process comprising one of sorting, sieving, separating, purifying, and the like of the nanomoieties prior to introducing the nanomoieties in the delivery medium to the binding sites. Many deterministic locations may be present on the surface of a substrate, enabling the formation or well-ordered arrays of oriented nanomoieties (e.g., nanoscale mandrels or nanotubes, nanorods, nanowires, or nanofibers) having a tight distribution of properties, where the density of the array can be controlled. Each element of the array can have a well-defined orientation and a deterministic location on the surface of the substrate, and such arrays may be used for a variety of purposes. The methods of this example are suitable for building arrays of nanopores, and variations on the methods of this example are suitable for building arrays of nanoscale transistors where the length of each nanoscale transistor is substantially perpendicular to the substrate surface.

By way of another example, some embodiments provide for placing a nanomoiety, for example, a silicon nanowire, at a deterministically located binding site, the binding site having an orienting characteristic (e.g., dimensional aspects or chemical, biological, and/or physical features that cause a certain orientation) by providing a location layer atop a substrate, the location layer being on the order of about 5 nm thick and having a binding site. The binding site can be a groove about 50 nm wide and about 750 nm long extending through the location layer to a portion of the substrate having a binding characteristic and comprising a binding patch.

Next, a delivery vehicle having an orientable characteristic (e.g., dimensional aspects or chemical, biological, and/or physical features that cause a certain orientation) is disposed at the binding site by exposing the location layer and the substrate to a delivery medium including a liquid solution containing a plurality of delivery vehicles, each such delivery vehicle being coupled to a nanomoiety payload. The delivery vehicle may include, but is not limited to, a protein-based nanorod coupled to a silicon nanowire by organosilane chemistry and surrounding the nanowire. The nanorod may have a diameter of, for example, about 30-45 nm so that only one delivery vehicle can fit within a groove about 50 nm wide and reach the binding patch.

The delivery vehicle also has a binding region for binding the delivery vehicle to the binding patch. For example the substrate may include silicon dioxide, the binding patch may be occupied by a layer of oligonucleotides coupled to the substrate by an organosilane layer, and the cylindrical wall aspect of the nanorod may comprise a binding region decorated with oligonucleotides complementary to the oligonucleotides in the binding patch.

The location layer may include an electron beam resist with a low non-specific binding affinity for the binding region of the delivery vehicle. The delivery medium may comprise water, for example, containing a plurality of delivery vehicles. Thermal diffusion of the delivery vehicle in the delivery medium results in the delivery vehicle binding to the oligonucleotides at the binding patch. Once the delivery vehicle is in place at the binding site the delivery medium is removed, and any remaining unbound delivery vehicles are washed away.

In an embodiment, the location layer may be removed, for example by washing in a solvent, advantageously removing any delivery vehicles that have undesirably bound to the location layer surface by nonspecific binding. The substrate may then be heated in a reducing atmosphere, for example, serving to cause silicon-to-oxide bonds to occur at the region where the nanowire adjoins the silicon dioxide substrate and serving to volatilize organic compounds. The nanowire is left in place on the silicon dioxide substrate and can subsequently be covered with a gate insulator by, for example, atomic layer deposition, and fabrication of a nanowire transistor can proceed by using known techniques to form gate, source, and drain electrodes.

Advantageously in this example, the delivery vehicle may include a reporter entity (e.g., a fluorophore or a quantum dot or radioactive particle) to indicate successful disposition of the nanomoiety at the binding site.

Further, the nanomoieties may advantageously have a tight distribution of properties achieved through a process including one of sorting, sieving, separating, purifying, and the like, of the nanomoieties prior to introducing the nanomoieties in the delivery medium to the binding sites.

Many deterministic locations may be present on the surface of a substrate, enabling the formation or well-ordered arrays of oriented nanomoieties (e.g., nanoscale mandrels or nanotubes, nanorods, nanowires, or nanofibers) having a tight distribution of properties, where the density of the array can be controlled. Each element of the array can have a well-defined orientation and a deterministic location on the surface of the substrate, and such arrays may be used for a variety of purposes.

The methods of this example are suitable for building arrays of nanoscale transistors where the length of each nanoscale transistor lies parallel to the substrate surface and the location of each nanowire is well controlled. In particular, each such nanotransistor may include multiple nanowires in parallel connection, sharing common gate, source, and drain electrodes, to increase current carrying capability of the transistor.

In a first embodiment of the method, a structure having a location layer (e.g., about 200 nm thick) is disposed atop a substrate. The location layer has a location feature (e.g., a nanoscale hole or pit of about 50 nm in diameter and extending through the thickness of the location layer) being at a deterministic location defined by known methods, for example electron beam lithography. The exposed portion of the substrate at the bottom of the location feature includes a binding patch having a binding characteristic.

The structure is introduced to a delivery medium including a solution having a nanoscale delivery vehicle. The delivery vehicle is coupled to a nanomoiety, for example a seed particle, and has a binding region on all or a portion of its exposed surface. The nanomoiety and the delivery vehicle may be a unitary system wherein the nanomoiety may exist in potential only, comprising a part of the delivery vehicle to be rendered from the delivery vehicle by a subsequent process such as, but not limited to, removal, reaction, oxidation, and/or reduction of the delivery vehicle. For example, where it is desired to place a nanomoiety comprising an iron oxide seed particle at a binding site, the seed particle may be created by oxidizing iron atoms in the delivery vehicle during a rendering process, and the iron atoms and the delivery vehicle may comprise a unitary element before the subsequent rendering process.

The delivery vehicle moves into the hole, for example via the random motion characteristic of diffusion in a liquid. A binding region on the delivery vehicle has an affinity for the binding patch, and when it contacts the binding patch it attaches thereto. The delivery vehicle is small enough to fit into the hole but large enough to preclude any other delivery vehicle from binding at the binding patch. Any remaining unbound delivery vehicles are washed away. Subsequently, the nanomoiety is rendered from the delivery vehicle by methods such as, but not limited to, removing, reacting, oxidizing, and/or reducing. The nanomoiety has a retention characteristic which keeps it bound to the substrate after rendering. In another embodiment, the delivery vehicle is left in place, thereby leaving the nanomoiety bound to the substrate by the same mechanism that caused the binding of the binding region to the binding patch.

The location layer may be removed before or after rendering of the nanomoiety from the delivery vehicle.

If for example the nanomoiety comprises a nanoseed, the nanoseed may be used for further fabrication processes, for example in according with the teachings of (patent application Ser. No. 11/487,550, filed on Jul. 14, 2006) to form a nanopore or a nanoscale transistor or for other purposes.

To assist in the fabrication process, the delivery vehicle may also be coupled to a reporter entity, for example one or more fluorophores, one or more quantum dots, and/or one or more radioactive tracer particles. The reporter entity may be coupled to the delivery vehicle either before or after the delivery vehicle binds to the substrate. A reporter entity detection system can be employed to detect the reporter entity. The reporter entity system may employ mechanisms such as, but not limited to, a laser scanner, a camera, a photographic plate, and/or a confocal microscope.

For example, the reporter entity detection system can be used to ascertain if the nanomoiety is bonded or otherwise attached to the substrate. In addition, the reporter entity detection system can determine the location of the nanomoiety, and therefore the position at which, for example, a nanopore or nanoscale transistor is subsequently formed, thereby advantageously providing in-process yield information for the fabrication process.

In a second embodiment, a nanomoiety is both placed at a deterministic location and is placed in a well-defined orientation, for example, perpendicular to the top surface of the substrate. The method includes providing a structure having a location layer, for example about 200 nm thick, disposed on a substrate, where the location layer has a location and alignment feature. For example, the location and alignment feature can include, but is not limited to, a nanoscale hole, about 50 nm in diameter with substantially vertical walls and extending through the thickness of the alignment layer. The exposed portion of the substrate at the bottom of the hole includes a binding patch having a binding characteristic.

Then, the structure is introduced to a delivery medium including a solution having a nanoscale delivery vehicle, wherein the nanoscale delivery vehicle is associated to the nanomoiety to be placed, and the nanoscale delivery vehicle has a binding region. The nanomoiety may be, for example, a carbon nanotube having a length aspect much longer than its diameter aspect, for example a length of about 200 nm and a diameter on the order of about 1-10 nm. The delivery vehicle may have a diameter of, for example, about 35 nm and a length of, for example, about 100-500 nm.

The binding region of the delivery vehicle may occupy a single end of the delivery vehicle, or may occupy both ends, or may occupy a portion of the surface area aligned along the length of the delivery vehicle, or may occupy the entire surface of the delivery vehicle. The delivery vehicle moves into the hole, for example via a random motion characteristic of diffusion in a liquid. The binding region has an affinity for the binding patch, and when it contacts the binding patch it attaches thereto. Any remaining unbound delivery vehicles are washed away.

Subsequently, the location layer is removed and the nanomoiety is rendered from the delivery vehicle by methods such as, but not limited to, removing, reacting, oxidizing, and/or reducing. The nanomoiety has a retention characteristic that keeps it bound to the substrate after the rendering process.

In another embodiment, the delivery vehicle is left in place, leaving the nanomoiety attached to the substrate at a deterministic location and in a desired orientation, thereby leaving the nanomoiety bound to the substrate by the same mechanism which caused the binding of the binding region to the binding patch.

For a situation in which the nanomoiety is to be aligned perpendicular to the top surface of the substrate, the delivery vehicle can be designed to move into the location and alignment feature much as a loose-fitting cork would move into the neck of a bottle. For example, if the location and alignment feature is about 50 nm in diameter and about 200 nm deep, the delivery vehicle can be designed with a generally cylindrical aspect having a diameter on the order of about 30-45 nm and a length on the order of about 200 nm, and a binding region on one or both end regions of the delivery vehicle, so that only one delivery vehicle at a time can slide into the location and alignment feature, and only one delivery vehicle can bind the to substrate at the deterministic location of the location and alignment feature. This arrangement is suitable, for example, for producing nanoscale mandrel structures suitable for use in the methods taught in (patent application Ser. No. 11/487,550, filed on Jul. 14, 2006) or for other uses.

For a situation in which the nanomoiety is to be aligned parallel to the top surface of the substrate, the location and alignment feature can be designed as a long slot extending parallel to the surface of the substrate and extending through the thickness of the location and alignment layer, the slot having a width of, for example, about 50 nm and a length of, for example, about 250 nm. The delivery vehicle can be designed with a generally cylindrical aspect having a diameter of, for example, on the order of about 30-45 nm and a length of, for example, about 200 nm, with its associated binding region exhibiting a binding affinity for a binding patch on the substrate along the length of the delivery vehicle.

This arrangement is suitable, for example, for laying one or more carbon nanotubes across a source, a gate, and a drain region of a nanoscale transistor circuit in order to fabricate carbon nanotube transistors having a channel or channels parallel to the surface of the substrate.

To assist in the fabrication process, the delivery vehicle may also be coupled to a reporter entity, for example one or more fluorophores, one or more quantum dots, or one or more radioactive tracer particles. The reporter entity may be coupled to the delivery vehicle either before or after the delivery vehicle binds to the substrate. A reporter entity detection system can be employed to detect the reporter entity. For example, the reporter entity detection system can be used to ascertain if the nanomoiety is bonded or otherwise attached to the substrate, thereby advantageously providing in-process yield information for the fabrication process.

The following fabrication processes are not intended to be an exhaustive list that includes every step required for fabricating the nanopore substrate. In addition, the fabrication process is flexible because the process steps may be performed in a different order than the order illustrated in FIGS. 1A-7C.

FIGS. 1A through 1K are cross-sectional views that illustrate a representative method of fabricating a synthetic nanopore. FIG. 1A illustrates a structure 10 including a substrate 12 having a location layer 14 (also known as a location and alignment layer) disposed thereon. At least one nanoscale hole 16 is present that extends through the location layer 14 to expose the substrate 12. The substrate 12 can include materials such as, but not limited to, silicon, silicon dioxide, silicon nitride, polyimide, and polyether-ether-ketone (PEEK). A deterministically located nanoscale binding site 15 comprises the nanoscale hole 16 in the layer 14, the associated exposed area 17 of the substrate 12, and a binding patch 18 on the exposed area 17.

The location layer 14 can include materials such as, but not limited to, electron beam resist, polymers, insulators, semiconductors, metals, and/or materials that can be adherently placed on the substrate 12 in layer form and in which nanoscale holes can be defined by methods such as electron beam lithography, photolithography, x-ray lithography, ultraviolet lithography, focused ion beam machining, and etching. The location layer 14 can be about 2 nm to 2000 nm thick.

At least one nanoscale hole 16 (also referred to as a nanochannel or pit) is present through the location layer 14 (also referred to as the location and alignment layer) to expose the substrate 12 at a deterministic location including the exposed area 17 of the substrate 12 exposed at the bottom of nanoscale hole 16. The nanoscale hole 16 can have a diameter aspect of about 2 to 10 nm, about 5 to 50 nm, and about 10 to 100 nm. The nanoscale hole 16 can have a depth aspect of about 1 to 5 nm, about 2 to 10 nm, and about 5 to 2000 nm.

Figure 1D:
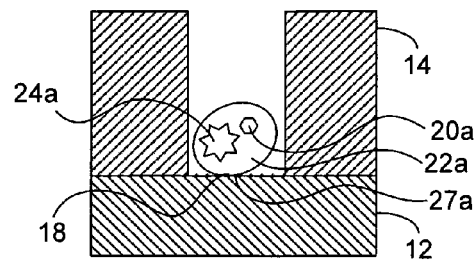
Figure 1B:
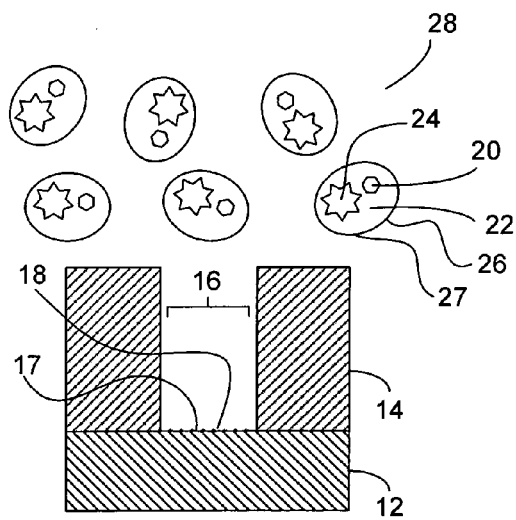

FIG. 1B illustrates a plurality of nanomoieties 20 in a delivery medium 28 surrounding the substrate 12. Each nanomoiety 20 is associated with a delivery vehicle 22 having a reporter entity 24. The surface 26 of the delivery vehicle 24 has a binding region 27 for binding to the binding site 28 at the bottom of the nanoscale hole 16.

The binding region 27 has an affinity for and attaches to or otherwise interacts (e.g., chemically, biologically, and/or physically) with the substrate 12 at the binding patch 18. One embodiment of the delivery vehicle 22 may have a binding region comprising a limited portion of its outer surface, may have multiple binding regions, or may have a binding region comprising its entire outer surface.

The nanomoiety 20 can be, but is not limited to, a seed particle for growing a nanomoiety such as a nanotube, nanorod, nanowire, and/or nanofiber.

The nanomoiety can have a diameter aspect of about 1 to 5 nm, about 2 to 10 nm, and about 5 to 50 nm. The nanomoiety 20 can have a length aspect of about 1 to 50 nm, about 2 to 100 nm, and about 2 to 500 nm.

The nanomoiety 20 may exist only in potential form during its association with the delivery vehicle 22. For example the delivery vehicle 22 may include a bioferritin protein molecule encapsulating about 2000 to 4500 iron atoms, and the nanomoiety 20 may be produced when the bioferritin molecule is subsequently removed, reacted, oxidized, reduced, or left in place, for example by heating in an oxidizing ambient, to produce a seed particle of iron oxide comprising the nanomoiety 20 at the deterministic location.

The delivery vehicle 22 can include, but is not limited to, a polymer, a biopolymer, a macromolecule, a bioferritin molecule, an encapsulated macromolecule, an agglomeration of dendrimers, and combinations thereof. The delivery vehicle 22 can have a diameter aspect of about 2 to 50 nm, about 5 to 100 nm, and about 2 to 500 nm. The delivery vehicle 24 can have a length aspect of about 5 to 50 nm, about 10 to 200 nm, and about 10 to 2000 nm.

The delivery vehicle 22 is coupled to the nanomoiety 20 in a fashion that may include, but is not limited to, encapsulation of the nanomoiety 20 by the delivery vehicle 22, adhesion between the nanomoiety 20 and the delivery vehicle 22, chemical bonding between the nanomoiety 20 and the delivery vehicle 22, and may include a unitary structure of the nanomoiety 26 and the delivery vehicle 22.

The delivery vehicle 22 functions to increase the size of the combination of the nanomoiety 20 and the delivery vehicle 22 so that only one nanomoiety 20 can be placed at each deterministic location even though the nanomoiety 20 is much smaller than the diameter aspect of the nanoscale hole 16. The delivery vehicle 22 has dimensional aspects that only allow one nanomoiety 20 to be able to interact with the substrate 12 at the binding patch 18 via the nanoscale hole 16. As such, the delivery vehicle 22 has dimensions that permit a single nanomoiety 20 to enter the nanoscale hole 16 and allow the single nanomoiety 20 to interact with the substrate 12 at the binding patch 18.

The dimensions of the delivery vehicle 22 depend, in part, on its three-dimensional shape. For example, if its three-dimensional shape is a sphere, its diameter should be less than the diameter aspect of the nanoscale hole 16, and its diameter aspect should also be greater than half the diameter of the nanoscale hole 16, which will allow only a single delivery vehicle 22 to reach the binding patch 18 at one time. If the delivery vehicle 22 is oblong or some other shape, then its smallest cross-sectional dimensions should be such that one, but only one, delivery vehicle 22 is able to interact with the binding patch 18 via the nanoscale hole 16 at one time.

The delivery vehicle 22 can have a diameter aspect of about 2 to 10 nm, about 5 to 50 nm, and about 1 to 100 nm. The delivery vehicle 22 can have a length aspect of about 2 to 10 nm, about 5 to 500 nm, and about 5 to 5000 nm.

The delivery vehicle 22 associated with the nanomoiety 20 includes a reporter entity 24 that has a detectable characteristic that allows the presence and/or the position of the nanomoiety 22 to be ascertained (e.g., detected using a detection system). Including a reporter entity 24 (shown as a "star" in the figures) can be used to verify that a nanomoiety 20 is located at a particular position, which can be used in validating that, for example, a nanopore can later be formed at that position and/or that the fabrication process is proceeding properly. The reporter entity can include, but is not limited to, a quantum dot, a chromophore, a fluorophore, a lumophore, a dye, and combinations thereof.

Figure 1E:
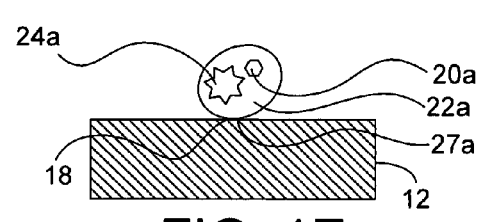
Figure 1F:
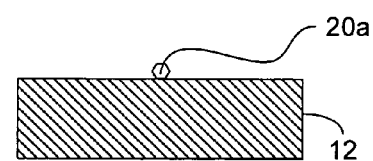
Figure 1C:
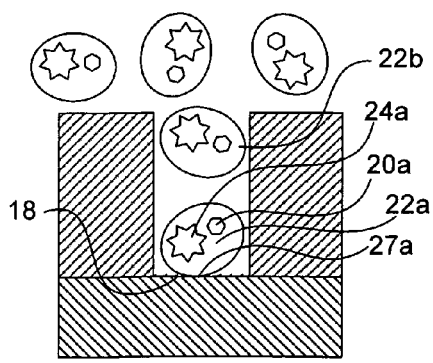

FIG. 1C illustrates a single delivery vehicle 22a interacting with the substrate 12 at the binding patch 18, while a second delivery vehicle 22b is excluded from such interaction by the size of delivery vehicle 22a. The binding region 27a is attached or otherwise interacts (e.g., chemically, biologically, and/or physically) with the binding patch 18.

FIG. 1D illustrates the single delivery vehicle 22a bound to the substrate 12 at the binding patch 18 after the removal of the remaining unbound delivery vehicles 22. At the stage shown in FIG. 1E the reporter entity 24a can be read, for example via a scanner, to verify that the delivery vehicle 22a is bound in place at binding patch 18.

FIG. 1E illustrates the single delivery vehicle 22a bound to the substrate 12 at the binding patch 18 after the removal of the location layer 14. The location layer 14 can be removed using techniques such as, but not limited to, solvent washing, caustic etching, ozone stripping, and plasma etching. Advantageously in some cases, the step of rendering the nanomoiety from the delivery vehicle can be combined with removal of the location layer 14. Also advantageously in some cases, the step of removing the location layer 14 can serve to remove any undesirable bound delivery vehicles from sites other than the desired binding sites. At the stage shown in FIG. 1E the reporter entity 24a can be read to verify that that the delivery vehicle 22a is bound in place at binding patch 18.

Figure 1G:
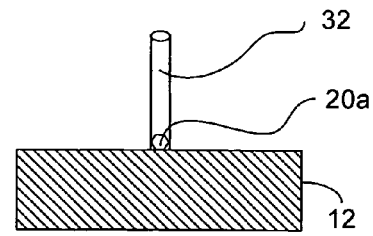

FIG. 1F illustrates the nanomoiety 20a bound in place via a retention characteristic, not shown, after rendering (e.g., removing, reacting, oxidizing, and/or reducing) of the nanomoiety 20a from the delivery vehicle 22a FIG. 1G illustrates a mandrel 32 fabricated using the nanomoiety 20a where, for example, the nanomoiety 20a is a seed particle (nanoseed) for fabricating the mandrel 32 as a carbon nanotube. The mandrel 32 is substantially perpendicular to the substrate surface 12, so that the mandrel 32 stands straight up as shown in FIG. 1G. Such perpendicularity can be achieved, for example, by using known techniques of applying an electric field during growth of carbon nanotube. In some embodiments as in FIG. 1G the mandrel 32 may be such a nanotube, while it other embodiments the mandrel 32 may be a nanowire, nanowhisker, or nanorod. In some cases the nanomoiety 20a remains in place on the substrate 12 when the mandrel is grown using the nanomoiety 20a as a seed, while in other cases the nanoseed positions itself atop the mandrel as it grows, becoming detached from the substrate 12; that case is not illustrated in FIG. 1G.

The mandrel 32 can be fabricated using techniques such as, but not limited to, field-enhanced plasma deposition, plasma-enhanced chemical vapor deposition, chemical vapor deposition, and molecular beam epitaxy. In another embodiment, a reporter molecule, not shown, can be attached to the mandrel 32 after it is grown. The mandrel 32 can be a structure such as, but not limited to, a single-walled carbon nanotube, a multiwalled carbon nanotube, a semiconductor nanowire, and a semiconductor nanorod. The diameter of the mandrel 32 can be about 1 to 100 nm. The length of the mandrel 32 can be about 2 to 5000 nm, or it may extend to an indefinite length of many micrometers.

Figure 1H:
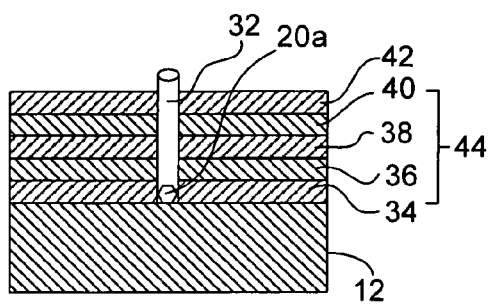

FIG. 1H illustrates the sequential fabrication of a plurality of layers 34, 36, 38, 40, and 42 to form a nanopore substrate 44 around the mandrel 32. For example, layer 34 may be an insulator layer deposited on the substrate 12, layer 36 a conductor layer deposited on layer 34, layer 38 an insulator layer deposited on layer 36, layer 40 a conductor layer deposited on layer 38, and layer 42 an insulator layer deposited on layer 40, thereby facilitating the construction a nanopore surrounded by two resonant tunneling electrodes with insulators atop and beneath each electrode. The number of layers can vary and the materials used to make the layers can vary as well. The layers of the nanopore substrate 44 should be constructed with the intent of creating a functioning nanopore substrate 44. The nanopore substrate 44 can include, but is not limited to, detection electrodes, (e.g., resonant tunneling electrodes as described above), detection integrated circuitry, and the like. The layers 34, 36, 38, and 42 can be made of materials such as, but not limited to, silicon nitride, silicon oxide, silicon dioxide, aluminum oxide, platinum, iridium, and polyimide, as well as appropriate materials to produce the detection electrodes and the detection integrated circuitry.

Figure 1J:
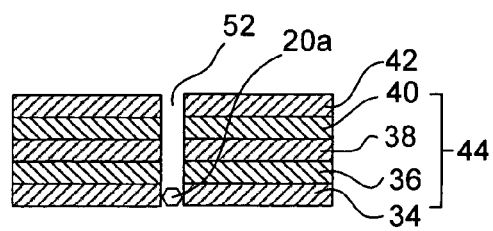
Figure 1I:
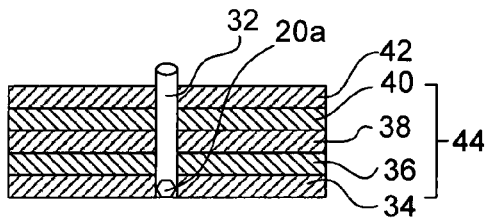

FIG. 1I illustrates the nanopore substrate 44 after removal of the substrate 12. The substrate 12 can be removed using techniques such as, but not limited to, chemical etching, ion cutting, mechanical lapping, and chemomechanical polishing.

FIG. 1J illustrates the nanopore substrate 44 after removal of the mandrel 32. The mandrel 32 can be removed using techniques such as, but not limited to, oxygen plasma etching, ozone etching, oxidation, and firing. After the mandrel 32 is removed a nanopore 52 is left, extending through most of the nanopore substrate 44 but blocked at one end by the nanomoiety 20a.

Figure 1K:
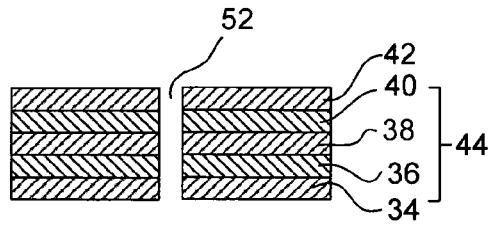

FIG. 1K illustrates the removal of the nanomoiety 20a from the nanopore substrate 44 to clear the nanopore 52. The nanomoiety 20a can be removed using techniques such as, but not limited to, phosphoric acid etching, plasma etching, and wet chemical etching. Additional fabrication steps can be performed to further refine the nanopore substrate 44, for example to make proper electronic connections so that measurements can be made using the nanopore substrate 44 and the synthetic nanopore 52. Portions of the substrate 12 not shown in FIGS. 1A-1K may remain in the finished structure.

Figure 2A:
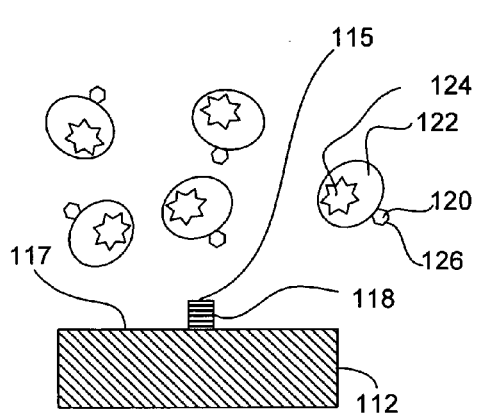
FIGS. 2A through 2L are cross-sectional views that illustrate another representative method of placing a nanomoiety on a substrate at a deterministically located binding site and employing the nanomoiety in fabricating a synthetic nanopore.

FIGS. 2A through 2L are cross-sectional views that illustrate a representative method of placing a nanomoiety 120 on a substrate 112 at a deterministically located binding site 115. FIG. 2A illustrates a structure having a substrate 112, which has surface 117 having a binding patch 118 disposed thereon, the binding patch 118 illustrated as having some thickness, although that is not a necessity. The substrate 112 can include materials such as, but not limited to, silicon, silicon dioxide, silicon nitride, polyimide, and polyether-ether-ketone (PEEK).

The binding patch 118 can include materials such as, but not limited to, an organosilane, a thiolated organosilane, an oligonucleotide chain, and a protein that can be adherently placed on the substrate 112 in layer that the nanomoiety can attach to. The binding patch 118 can be about 2 nm to 2000 nm thick. In other embodiments, the binding patch can be flush with the surface 117, or it can be recessed from the surface 117.

In addition, FIG. 2A illustrates a plurality of nanomoieties 120 introduced to the substrate 112. Each nanomoiety 120 is coupled to a delivery vehicle 122. A binding region 126 is illustrated as occupying one surface of the nanomoiety 120. As an alternative, not shown, the binding region 126 could occupy a region of the surface of the delivery vehicle 122. As another alternative, not shown, the nanomoiety 120 can be incorporated entirely within the surface of the delivery vehicle 122. As another alternative, not shown, the nanomoiety 120 can be partly within and partly protruding from the surface of the delivery vehicle 122. The nanomoiety 120 may comprise a long structure and the delivery vehicle 122 may comprise a widened bulbous structure near one end of the nanomoiety 120.

The binding region 126 has an affinity for and attaches or otherwise interacts (e.g., chemically, biologically, and/or physically) with the binding patch 118. One embodiment of the delivery vehicle 122 may have multiple binding regions, or may have a binding region occupying its entire surface. The delivery vehicle 122 and the nanomoiety 120 may comprise a unitary structure. The lateral extents of binding patch 118 may be defined by available techniques such as, for example, electron beam lithography or dip pen nanolithography or stamp pad lithography to be, for example, in the range of 10-50 nm.

The nanomoiety 120 can be, but is not limited to, a nanotube, nanorod, nanowire, and/or nanofiber, or a seed particle for growing a nanostructure such as a nanotube, nanorod, nanowire, and/or nanofiber. The nanomoiety 120 can have a diameter aspect of about 1 to 10 nm, about 5 to 20 nm, and about 5 to 50 nm. The nanomoiety 120 can have a length aspect of about 2 to 10 nm, about 5 to 100 nm, and about 5 to 5000 nm.

The nanomoiety 120 may exist only in potential form during its association with the delivery vehicle 122. For example the delivery vehicle 122 may include a bioferritin protein molecule encapsulating about 2000 to 4500 iron atoms, and the nanomoiety 120 may be produced when the bioferritin molecule is subsequently removed, reacted, oxidized, reduced, or left in place, for example by heating in an oxidizing ambient, to produce a seed particle of iron oxide at the deterministic location.

The delivery vehicle 122 can include, but is not limited to, a polymer, a biopolymer, a macromolecule, a bioferritin molecule, an encapsulated macromolecule, an agglomeration of dendrimers, a peptide, a protein, a nucleic acid, and combinations thereof. The delivery vehicle 122 can have a diameter aspect of about 20 to 50 nm, about 2 to 100 nm, and about 20 to 500 nm. The delivery vehicle 122 can have a length aspect of about 2 to 50 nm, about 2 to 500 nm, and about 2 to 5000 nm.

The delivery vehicle 122 is coupled to the nanomoiety 120 in a fashion that may include, but is not limited to, encapsulation of the nanomoiety 120 by the delivery vehicle 122, adhesion between the nanomoiety 120 and the delivery vehicle 122, chemical bonding between the nanomoiety 120 and the delivery vehicle 122, and may include a unitary structure of the nanomoiety 120 and the delivery vehicle 122.

Figure 2B:
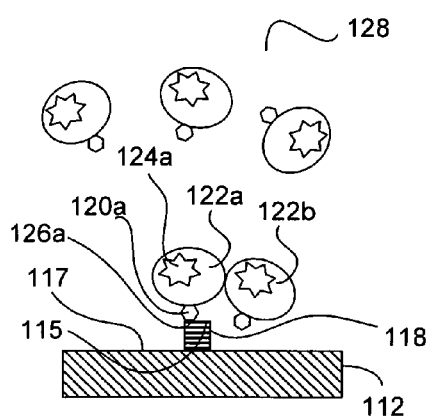

FIG. 2B illustrates a single delivery vehicle 122a in a delivery medium 128 interacting with the substrate 112 at the binding site 115. The binding region 126a of the nanomoiety 120a is attached to or otherwise interacts (e.g., chemically, biologically, and/or physically) with the substrate 112 via the binding patch 118. Advantageously, the shape and size of the delivery vehicle 122a are such, in relation to the lateral extents of the binding patch 118, that as it interacts with the binding patch 118 it "shoulders aside" other delivery vehicles such as delivery vehicle 122b, so that delivery vehicle 122b cannot bind.

Figure 2C:
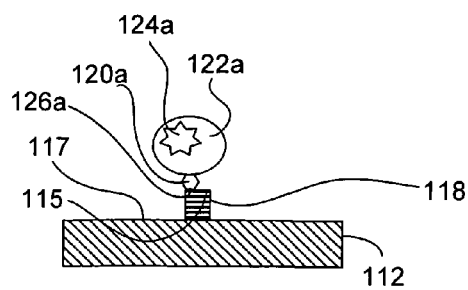

FIG. 2C illustrates the single delivery vehicle 122a bound to the binding patch 118 after the removal of the other delivery vehicles 122.

Figure 2D:
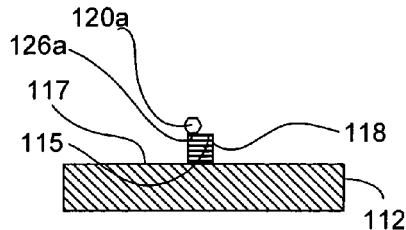

FIG. 2D illustrates the nanomoiety 120a bound to the bind patch 118 after rendering (e.g., removing, reacting, oxidizing, and/or reducing) of the nanomoiety 120a from the delivery vehicle 122a. The nanomoiety 120a has a retention characteristic for the substrate 112 after rendering, which may be the same as the binding characteristic that originally bound the binding region 126a to the binding patch 118.

Figure 2E:
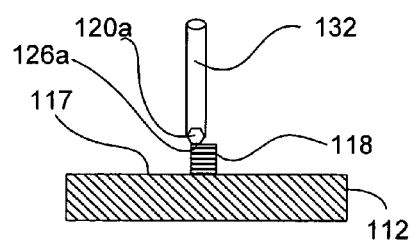
Figure 2F:
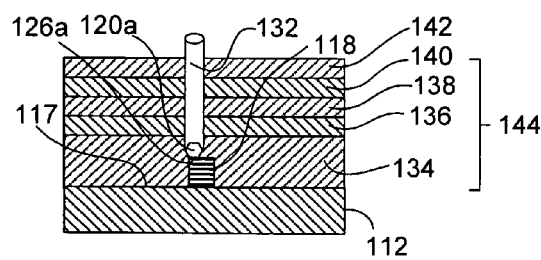

FIG. 2E illustrates the fabrication of a nanoscale mandrel 132 using the nanomoiety 120a as a nanoseed. The mandrel 132 is substantially perpendicular to the substrate surface 112, so that the mandrel 132 stands straight up as shown in FIG. 2E.

The mandrel 132 can be fabricated using techniques such as, but not limited to, field-enhanced plasma deposition, plasma-enhanced chemical vapor deposition, chemical vapor deposition, and molecular beam epitaxy. In another embodiment, a reporter molecule, not shown, can be attached to the mandrel 132 after it is grown. The mandrel 132 can be a structure such as, but not limited to, a single-walled carbon nanotube, a multiwalled carbon nanotube, a semiconductor nanowire, and a semiconductor nanorod. The diameter of the mandrel 132 can be about 1 to 100 nm. The length of the mandrel 132 can be about 2 to 5000 nm, or it may extend to an indefinite length of many micrometers.

Figure 2G:
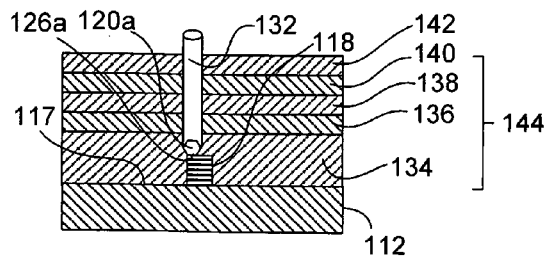

FIGS. 2F through 2K illustrate the use of the mandrel 132 on the substrate 112 to fabricate a nanopore, for example to be employed in DNA sequence identification. The use of the mandrel begins as illustrated in FIG. 2G with fabrication of a plurality of layers 134, 136, 138, 140, and 142 to form a nanopore substrate 144 around the mandrel 132. For example layer 134 may be an insulator, layer 136 a metal, layer 138 an insulator, layer 140 a metal, and layer 142 an insulator, thereby facilitating the fabrication of a nanopore having two metal resonant tunneling electrodes with insulators atop and beneath each electrode. The number of layers can vary and the materials used to make the layers can vary as well. The layers of the nanopore substrate 144 should be constructed with the intent of creating a functioning nanopore substrate 144. The nanopore substrate 144 can include, but is not limited to, detection electrodes (e.g., resonant tunneling electrodes as described above), detection integrated circuitry, and the like. The layers 134, 136, 138, 140, and 142 can be made of materials such as, but not limited to, silicon nitride, silicon oxide, silicon dioxide, aluminum oxide, platinum, iridium, and polyimide, as well as appropriate materials to produce the detection electrodes and the detection integrated circuitry.

Figure 2H:
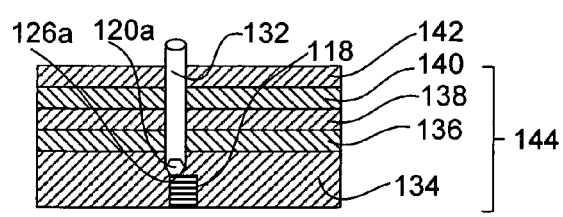

FIG. 2H illustrates the nanopore substrate 144 after removal of the substrate 112. The substrate 112 can be removed using techniques such as, but not limited to, chemical etching, ion cutting, mechanical lapping, and chemomechanical polishing. The figure shows the binding patch 118 remaining in place at this step, although this is not a necessity and the binding patch 118 may be removed in the same operation that removes the substrate 112.

Figure 2K:
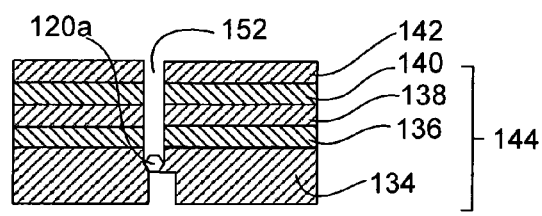
Figure 2I:
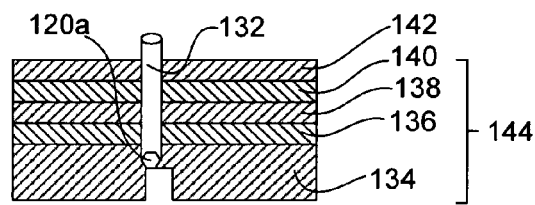

FIG. 2I illustrates the nanopore substrate 144 after removal of the binding patch 118. The binding patch 118 may be removed using techniques such as, but not limited to, plasma etching, ozone etching, reactive ion etching, and wet chemical etching FIG. 2K illustrates nanopore substrate 144 after removal of the mandrel 132. The mandrel 132 can be removed using techniques such as, but not limited to, oxygen plasma etching, ozone etching, oxidation, and firing. After the mandrel 132 is removed a nanopore 152 is left, extending through most of the nanopore substrate 144 but blocked near one end by the nanomoiety 120a.

Figure 2L:
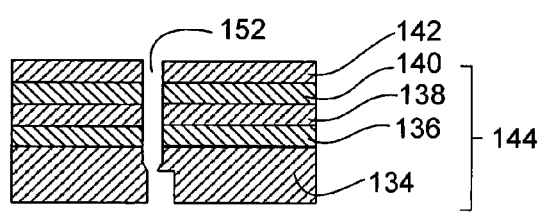
Figure 2J:
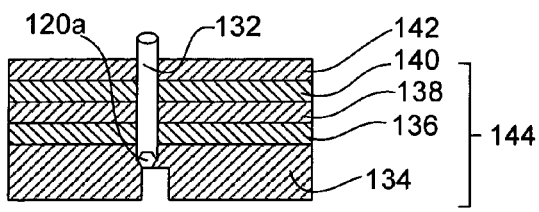

FIG. 2L illustrates the nanopore substrate 144 after removal of the nanomoiety 120a to clear the synthetic nanopore 152. The nanomoiety 120a can be removed using techniques such as, but not limited to, phosphoric acid etching, plasma etching, and wet chemical etching. Additional fabrication steps can be performed to further refine the nanopore substrate 144, for example to make proper electronic connections so that measurements can be made using the nanopore substrate 144 and the synthetic nanopore 152. Portions of the substrate 112 not shown in FIGS. 2A-2K may remain in the finished structure.

Figure 3A:
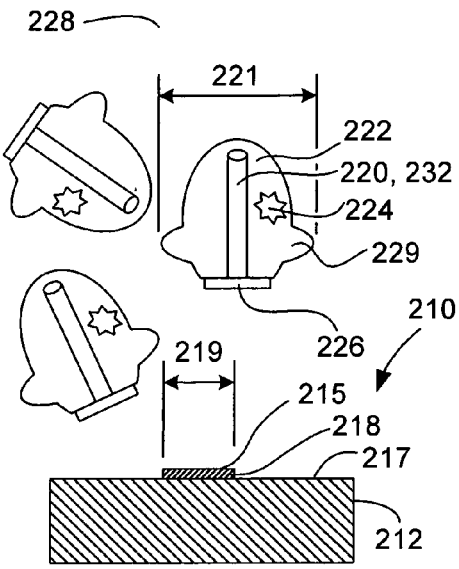
FIGS. 3A through 3D are cross-sectional views that illustrate a representative method of placing a nanomoiety on a substrate when a third characteristic dimension of a delivery vehicle is greater than a second characteristic dimension of a binding site and orientation of the nanomoiety perpendicular to the substrate is desired.

FIGS. 3A through 3D are cross-sectional views that illustrate a representative method of placing a nanomoiety on a substrate when a third characteristic dimension 221 of a delivery vehicle is greater than a second characteristic dimension 219 of a binding site and orientation of the nanomoiety perpendicular to the substrate is desired. FIG. 3A illustrates a structure 210 having a substrate 212, which has a binding patch 218 disposed on the surface 217 at a binding site 215. The substrate 212 can include materials such as, but not limited to, silicon, silicon dioxide, silicon nitride, polyimide, and polyether-ether-ketone (PEEK).

The binding patch 218 can include materials such as, but not limited to, an organosilane, a thiolated organosilane, a protein, and an oligonucleotide that can be adherently placed on the substrate 212 and that a nanoscale delivery vehicle 222 can attach to at a binding region 226. The binding patch 218 is shown as having a thickness. In other embodiments, the binding patch may be flush with the surface 217 or recessed from the surface 217. The binding patch may be, for example, a circle having a diameter comprising the second characteristic dimension 219

In addition, FIG. 3A illustrates a plurality of nanomoieties 220 and delivery vehicles 222 in a delivery medium 228 introduced to the structure 210. Each nanomoiety 220 is coupled to a delivery vehicle 222 and may be, for example, a nanotube or nanorod 232. The binding region 226 has an affinity for and can attach or otherwise interact (e.g., chemically, biologically, and/or physically) with the binding patch 218. The delivery vehicle 222 and the nanomoiety 220 may comprise a unitary structure.

The nanomoiety 220 can be, but is not limited to, a nanotube, a nanorod, a nanowire, and/or a nanofiber. The nanomoiety 220 can have a diameter aspect of about 1 to 10 nm, about 20 to 50 nm, and about 1 to 100 nm. The nanotube 232 can have a length aspect of about 2 to 10 nm, about 5 to 500 nm, and about 2 to 2000 nm.

The delivery vehicle 222 can include, but is not limited to, a polymer, a biopolymer, a macromolecule, a bioferritin molecule, an encapsulated macromolecule, an agglomeration of dendrimers, and combinations thereof.

The delivery vehicle 222 can have a diameter aspect of about 2 to 50 nm, about 5 to 100 nm, and about 2 to 200 nm. The delivery vehicle 224 can have a length aspect of about 2 to 100 nm, about 5 to 200 nm, and about 2 to 4000 nm.

The delivery vehicle 222 is coupled to the nanomoiety 220 in a fashion that may include, but is not limited to, encapsulation of the nanomoiety 220 by the delivery vehicle 222, adhesion between the nanomoiety 220 and the delivery vehicle 222, chemical bonding between the nanomoiety 220 and the delivery vehicle 222, and may include a unitary structure of the nanomoiety 220 and the delivery vehicle 222.

The binding region 226 on the delivery vehicle 222 occupies a limited portion of the surface of the delivery vehicle 222 near one end of the nanomoiety 220. The binding region may be attached to the delivery vehicle 222, to the nanomoiety 220, and/or to both the delivery vehicle 222 and the nanomoiety 220. A protrusion 229 near the binding region 226 has utility in shouldering aside other delivery vehicles during binding of the binding region 226 to the binding patch 218.

The delivery vehicle 222 may include a reporter entity 224 having uses similar to those of reporter entities described elsewhere in this disclosure.

Figure 3C:
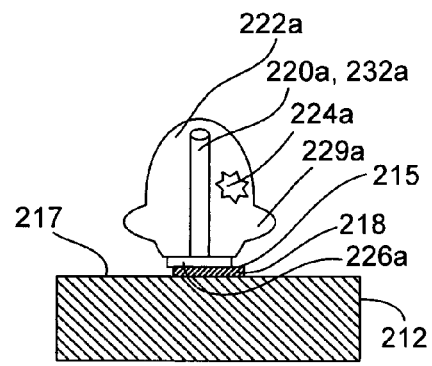
Figure 3B:
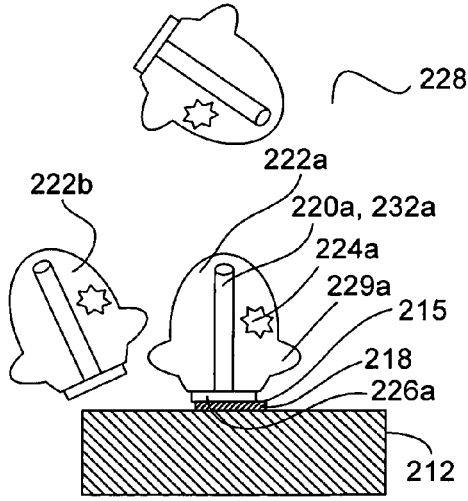

FIG. 3B illustrates a single delivery vehicle 222a interacting with the binding patch 218. The delivery vehicle 222a is attached or otherwise interacts (e.g., chemically, biologically, and/or physically) with the binding patch 218 via the binding region 226a. The third characteristic dimension 221a (not shown, but corresponding to the third characteristic dimension 221 in FIG. 3A) of the delivery vehicle 222a is large enough in relation to the second characteristic dimension 219 as shown in FIG. 3A that another delivery vehicle 222b cannot bind to the binding patch 218.

FIG. 3C illustrates the single delivery vehicle 222a bound to the substrate 212 at the binding patch 218 after the removal of the other nanomoieties 222.

Figure 3D:
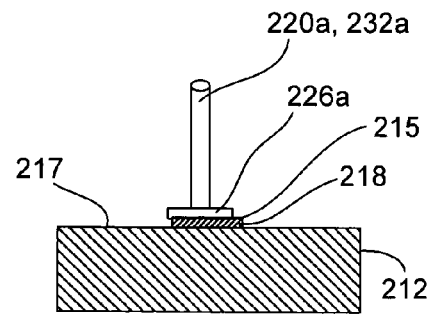

FIG. 3D illustrates the nanomoiety 220a retained on the substrate 212 after rendering (e.g., removing, reacting, oxidizing, and/or reducing) of the nanomoiety 220a from the delivery vehicle 222a. The nanomoiety 220a has a retention characteristic that keeps it bound to the substrate after the rendering process. In the embodiment illustrated, the binding region 226a survives the rendering process and the retention characteristic is the same as the binding characteristic that bound binding region 226a to binding patch 218.

The exemplary nanotube or nanorod 232a is substantially perpendicular to the substrate surface 212, so that the nanotube or nanorod 232a stands straight up as shown in FIG. 3D. In another embodiment, a reporter molecule can be attached to the end of the nanomoiety 220a after the rendering process.

It should be noted that a plurality of layers could subsequently be formed to produce a nanopore in a manner as described in FIGS. 2F through 2L.

Figures 4A, 4B:
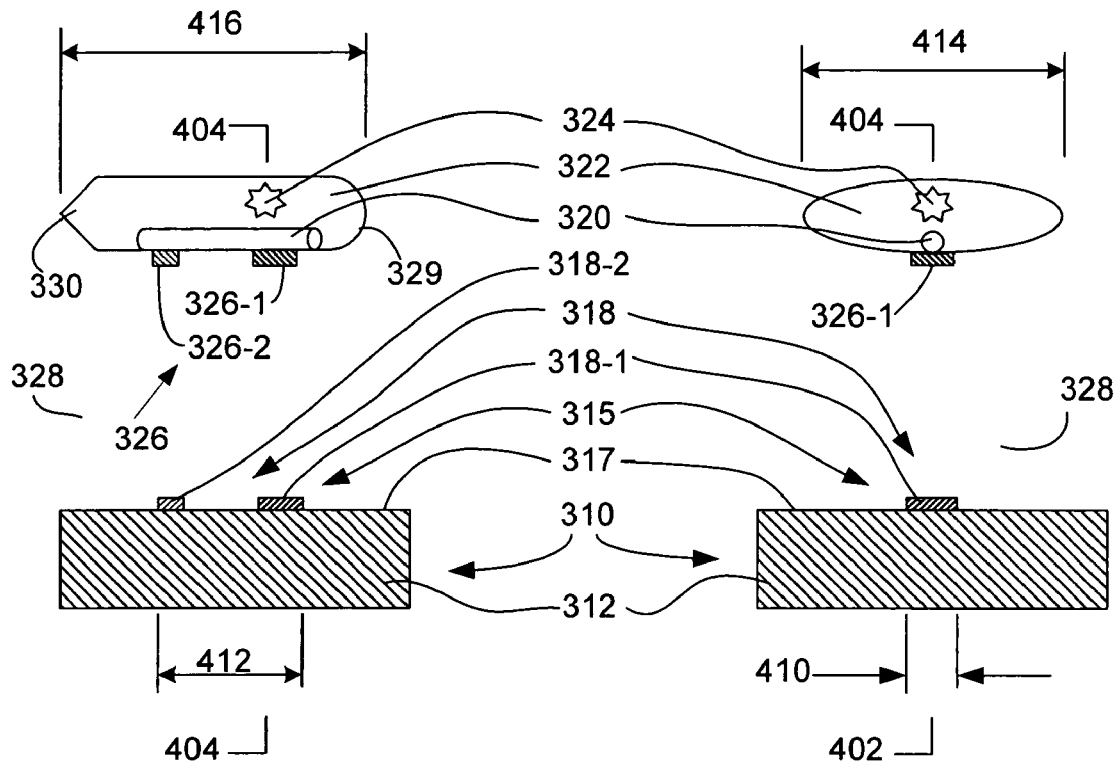
FIGS. 4A through 4F are cross-sectional views that illustrate a representative method of placing a nanomoiety on a substrate when a third characteristic dimension of a delivery vehicle is greater than a second characteristic dimension of a binding site and orientation of the nanomoiety parallel to the substrate is desired.

FIGS. 4A through 4F are cross-sectional views that illustrate a representative method of placing a nanomoiety on a substrate when a third characteristic dimension 321 of a delivery vehicle is greater than a second characteristic dimension 319 of a binding site and orientation of the nanomoiety parallel to the substrate is desired. FIGS. 4A and 4B are two views of the same volume, with FIG. 4A being a cross section drawn at section line 402-402 as shown in FIG. 4B and with FIG. 4B being a cross section drawn at section line 404-404 shown in FIG. 4A. Structure 310 is a structure having a substrate 312, the substrate 312 having a surface 317, the surface 317 having a binding site 315 disposed thereon, the binding site in this embodiment being a binding patch 318. The substrate 312 may be similar to the substrate 212 described above.

The binding patch 318 may advantageously be divided into two sections 318-1 and 318-2 having different binding characteristics.

A nanomoiety 320 having a generally cylindrical aspect is illustrated associated with a delivery vehicle 322 having a binding region 326 disposed on a limited area of its surface. The binding region 326 is advantageously divided into two sections 326-1 and 326-2 having different binding characteristics. Binding region section 326-1 has an affinity for binding patch section 318-1, and binding region section 326-2 has an affinity for binding patch section 318-2, while at the same time binding region section 326-1 does not have a binding affinity for binding patch section 318-2 and binding region section 326-2 does not have a binding affinity for binding patch section 318-1. Such an arrangement of two pairs of complementary binding affinities may be achieved, for example, by using two complementary sets of oligonucleotides as the binding means in binding region 318 and binding patch 326.

The delivery vehicle 322 may be one of many such delivery vehicles in a delivery medium 328 to which the surface 317 is exposed. The nanomoiety 320 associated with the delivery vehicle 322 has a length aspect having a length of, for example, about 250 nm, and a diameter aspect having a diameter of, for example, about 2 nm. The nanomoiety 320 can be, but is not limited to, a carbon nanotube, a semiconductor nanowire, or a nanorod. The diameter of the nanomoiety 320 comprises a first characteristic dimension for the purposes of this disclosure.

The binding patch 326 has a width aspect 410 as noted in FIG. 4B that comprises a second characteristic dimension for the purposes of this disclosure. In addition the binding patch 318 has a length aspect 412 as noted in FIG. 4A that comprises an additional second characteristic dimension for the purposes of this disclosure. Each of the width aspect 410 and the length aspect 412 is larger than the first characteristic dimension of the diameter of the nanomoiety 320. The width aspect 410 may be, for example, 20 nm wide, and the length aspect 412 may be, for example, 100 nm long.

The delivery vehicle 322 has a width aspect 414 as noted in FIG. 4B that comprises a third characteristic dimension for the purposes of this disclosure. In addition the delivery vehicle 322 as a length aspect 416 as noted on FIG. 4A that comprises an additional third characteristic dimension for the purposes of this disclosure. Each of the width aspect 414 and the length aspect 416 is larger than the diameter of the nanomoiety 320. The width aspect 414 may be, for example, about 200 nm wide and the length aspect 416 may be, for example, about 500 nm long.

Each of the width aspect 414 and the length aspect 416 of the delivery vehicle 322 are larger than each of the width aspect 410 and the length aspect 414 of the binding patch 318. Thus each of the third characteristic dimensions, as defined for the purposes of this disclosure, is larger than each of the second characteristic dimensions as defined for the purposes of this disclosure. This arrangement of sizes is advantageous in permitting one and only one delivery vehicle at a time to bind at the binding patch 318, equivalently in this embodiment at the binding site 315. In some cases the width aspect 414 of the delivery vehicle 322 can be smaller than length aspect 412 of the binding patch without departing from the spirit and scope of the present disclosure.

The arrangement of binding region sections and binding patch sections described above is advantageous in oriented binding of the delivery vehicle 322 in a chosen direction on the substrate 312, for example where the length aspect 414 of the delivery vehicle is oriented parallel to the length aspect 412 of the binding patch.

The delivery vehicle 322 can have distinguishable ends 329 and 330. When the delivery vehicle ends are oriented in one direction, for example with end 329 on the right and end 330 on the left as shown in FIG. 4A, the delivery vehicle can be said to have a particular polarity. The arrangement of binding region sections and binding patch sections described above is advantageous in oriented binding of the delivery vehicle 322 in a chosen direction, and with a chosen polarity, on the substrate 312. For example, binding may be performed where the length aspect 414 of the delivery vehicle is oriented parallel to the length aspect 412 of the binding patch, and where distinguishable end 329 is nearer to binding patch section 318-1 than to binding patch section 318-2, while distinguishable end 330 is nearer to binding patch section 318-2 than to binding patch section 318-1. The nanomoiety 320 can also have a polarity in its orientation, for example depicted by the ellipse at the right end of the nanomoiety in FIGS. 4A, 4C, and 4E, and so by its association with the delivery vehicle the nanomoiety 320 can be placed at a deterministically located site on substrate 312, with a particular orientation, with a particular polarity.

The one of the nanomoiety 320 and delivery vehicle 322 may also be associated with a reporter entity 324 having uses like those of reporter entities discussed elsewhere herein.

Figures 4C, 4D:
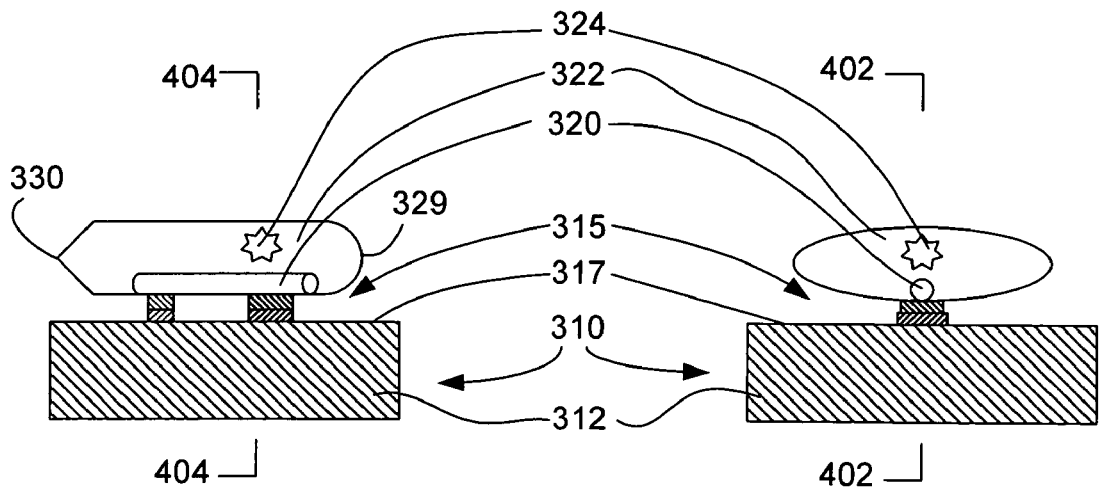

A single instance of delivery vehicle 322 in the delivery medium 328 can be stochastically bonded to the substrate 312 at binding site 315, while other delivery vehicles are excluded from the binding patch 318 by virtue of the size and shape of the delivery vehicle 322. FIGS. 4C and 4D illustrated the delivery vehicle 322 bonded to the substrate 312 after the delivery medium 328 has been removed and any remaining unbound delivery vehicles have been washed away.

Figures 4E, 4F:
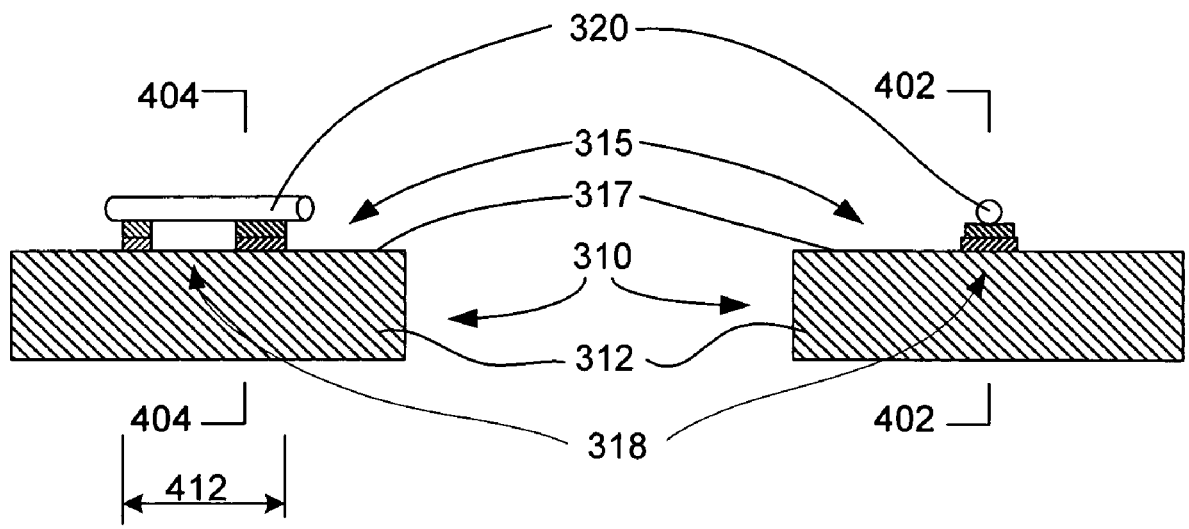

After binding of the delivery vehicle 322 to the substrate 312 at the binding site 315, the nanomoiety 320 can be rendered from the delivery vehicle to leave the nanomoiety bound in place. The nanomoiety has a retention characteristic that keeps it bound in place after then rendering process. FIGS. 4E and 4F illustrate the nanomoiety 320 bound in place after rendering, in an orientation parallel to the length aspect 412 of the binding patch 318, with a polarity depicted by the ellipse at the right end of the nanomoiety.

The nanomoiety 320 can be, but is not limited to, a nanotube, a nanorod, a nanowire, and/or a nanofiber. The nanomoiety 320 may comprise a unitary structure with the delivery vehicle 322. The nanomoiety 320 can have a diameter aspect of about 1 to 10 nm, about 2 to 50 nm, and about 1 to 100 nm. The nanomoiety 320 can have a length aspect of about 2 to 50 nm, about 5 to 500 nm, and about 2 to 1000 nm.

The delivery vehicle 322 can include, but is not limited to, a polymer, a biopolymer, a macromolecule, a bioferritin molecule, an encapsulated macromolecule, an agglomeration of dendrimers, and combinations thereof. The delivery vehicle 322 is designed with a binding region 326 where the exposed portion of the nanotube 262 can interact with the binding patch 218. For example, the binding region 326 may be a ring or rings surrounding the length aspect of the delivery vehicle 322 and/or may be regions of limited area along the bottom side of the length aspect 416 of the delivery vehicle as depicted in FIGS. 4A-4F.

The delivery vehicle 322 can have a width aspect 414 of about 5 to 100 nm, about 10 to 200 nm, and about 5 to 500 nm. The delivery vehicle 322 can have a length aspect 416 of about 10 to 100 nm, about 20 to 500 nm, and about 10 to 5000 nm.

The delivery vehicle 322 is coupled to the nanomoiety 320 in a fashion that may include, but is not limited to, encapsulation of the nanomoiety 320 by the delivery vehicle 254, adhesion between the nanomoiety 320 and the delivery vehicle 254, chemical bonding between the nanomoiety 320 and the delivery vehicle 254, and may include a unitary structure of the nanomoiety 320 and the delivery vehicle 254.

FIGS. 5A-5D are cross section views illustrating a method of placing a nanomoiety 520 at a deterministically located site 515 on a substrate 515 where it is desired for a length aspect of the nanomoiety 520 to be perpendicular to the surface 517 of the substrate 512. A delivery vehicle 522 is one of many such in a delivery medium 528 introduced to binding site 515.

A binding site 515 comprises a hole 516 in a location and alignment layer 514, the hole having near-vertical sidewalls, and a binding patch 518 on the surface 517 of the substrate 512.

The delivery vehicle 522 is associated with a nanomoiety 520 that can be useful as, for example, a mandrel 532 comprising one of a nanotube, a nanorod, and a nanowire. A binding region 526 occupies one end of the delivery vehicle in the embodiment illustrated, although in other embodiments binding regions may be on both ends or a binding region may occupy the entire surface of the delivery vehicle, or multiple binding regions may occupy multiple areas of the delivery vehicle.

A reporter entity 524 having utility like that of other reporter entities discussed herein may be associated with one of the delivery vehicle 522 and the nanomoiety 520.

When the binding site 515 is exposed to the delivery medium 528, the delivery vehicle 522 by chance happens to be the one delivery vehicle that slides to the bottom of the hole 516 like a loose-fitting cork, thereby precluding other delivery vehicles from sliding to the bottom of the hole 516, and with the particular orientation enabling binding region 526 to bind to the binding patch 518, thereby precluding any other delivery vehicle from binding to the binding patch 518.

Figure 5A:
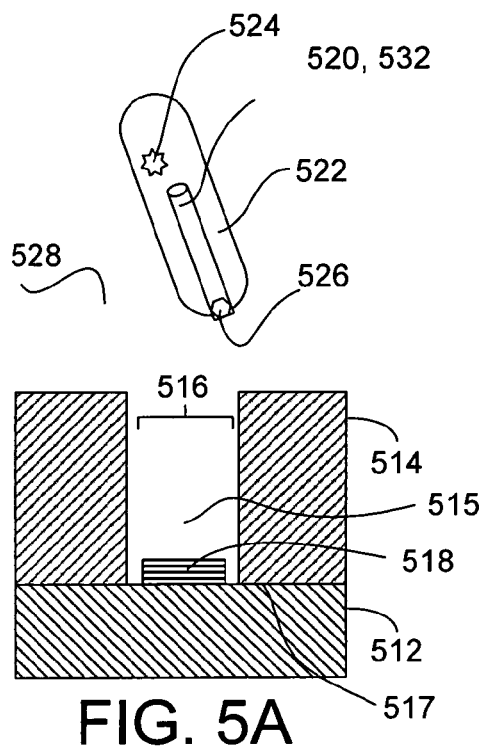
FIGS. 5A-5D are cross section views illustrating a method of placing a nanomoiety at a deterministically located site on a substrate where it is desired for a length aspect of the nanomoiety to be perpendicular to the surface of the substrate.
Figure 5C:
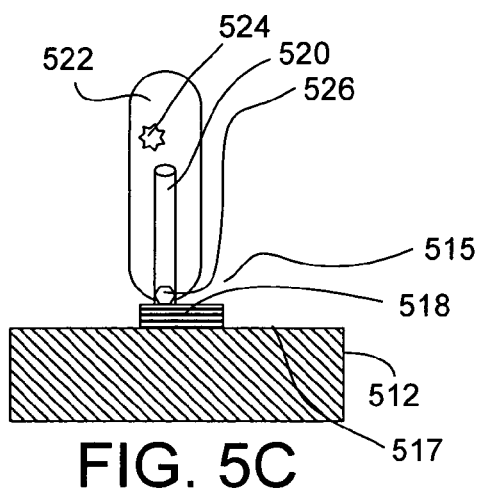
Figure 5B:
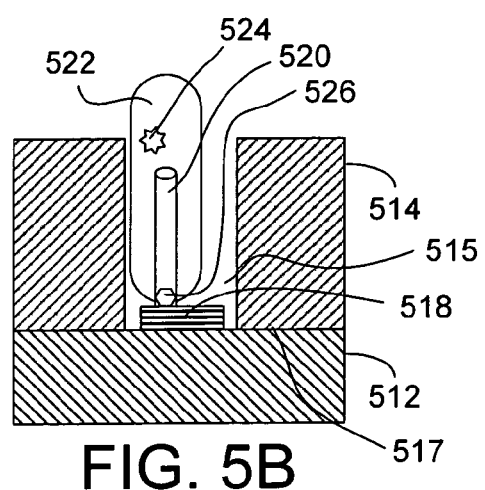

FIG. 5B illustrates the delivery vehicle bound in place at the binding site 515 after the delivery medium 528 has been removed and any unbound delivery vehicles have been washed away. The reporter entity 524 can be scanned to verify successful placement of the delivery vehicle 522 at the binding site 515.

FIG. 5C illustrates the delivery vehicle 522 bound in place after the location and alignment layer 514 has been removed. The removal of the location and alignment layer advantageously also removes any other delivery vehicles that had undesirably been bound to the location and alignment layer. At the stage shown in FIG. 5C the reporter entity 524 can be scanned to verify successful retention of the delivery vehicles at the binding site 515.

Figure 5D:
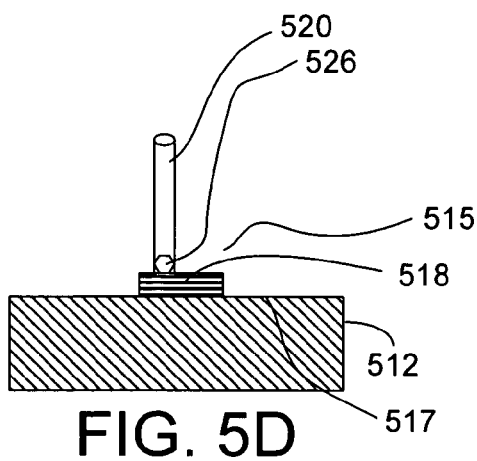

FIG. 5D illustrates the nanomoiety 520 retained in place after it has been rendered from the delivery vehicle 520 by a rendering process. The nanomoiety 520 has a retention characteristic that keeps it bound to the substrate after the rendering process. In the embodiment illustrated, the reporter entity 524 is gone at this stage. In other embodiments the reporter entity may be part of the nanomoiety, or a different reporter entity may subsequently be introduced to bind to the nanomoiety.

Figure 6A:
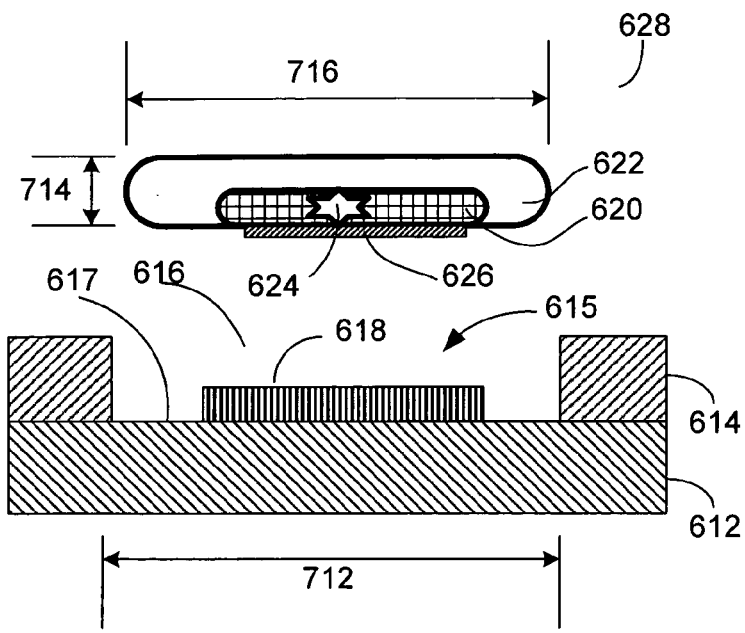
FIGS. 6A-6C and 7A-7C illustrate a method of placing a nanomoiety at a deterministically located bind site on a substrate where it is desired for a length aspect of the nanomoiety to be parallel to the surface of the substrate.
Figure 6B:
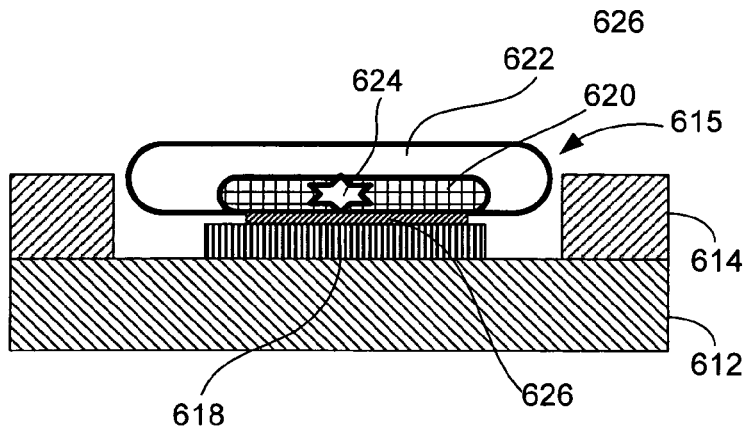
Figure 6C:
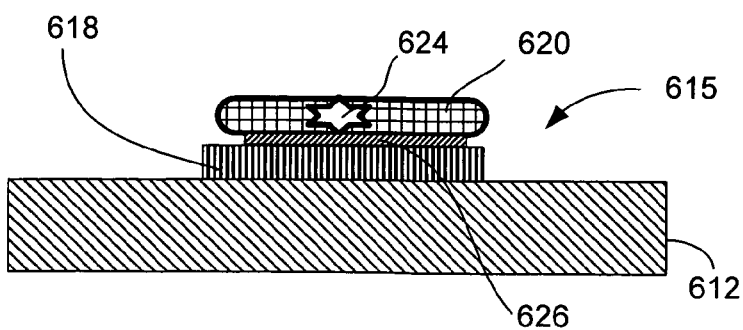
Figure 7A:
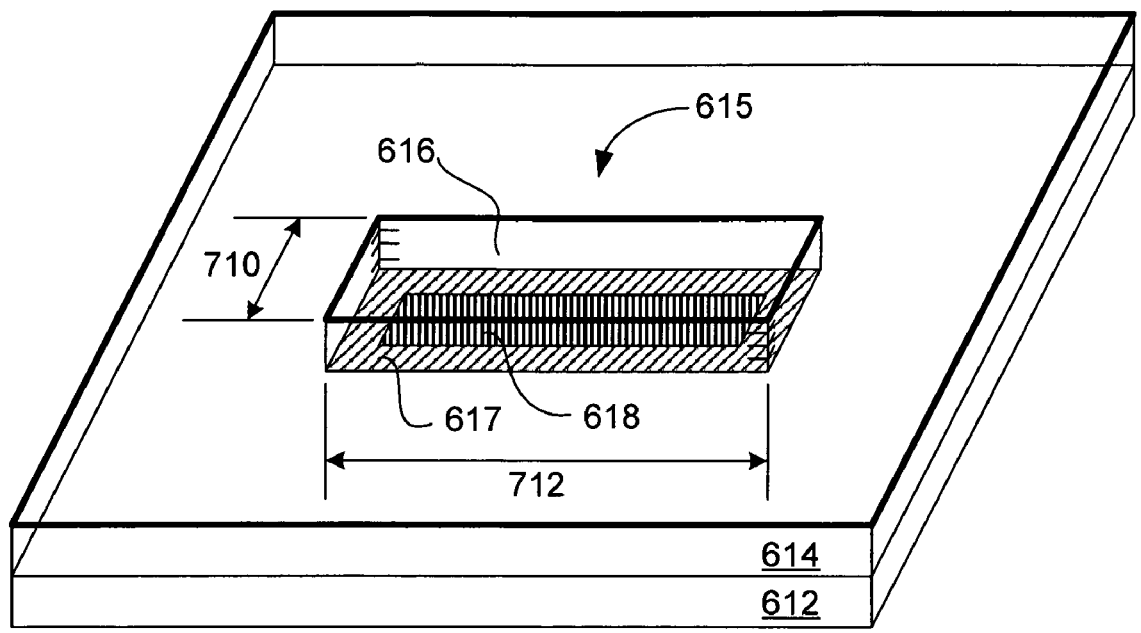
Figure 7B:
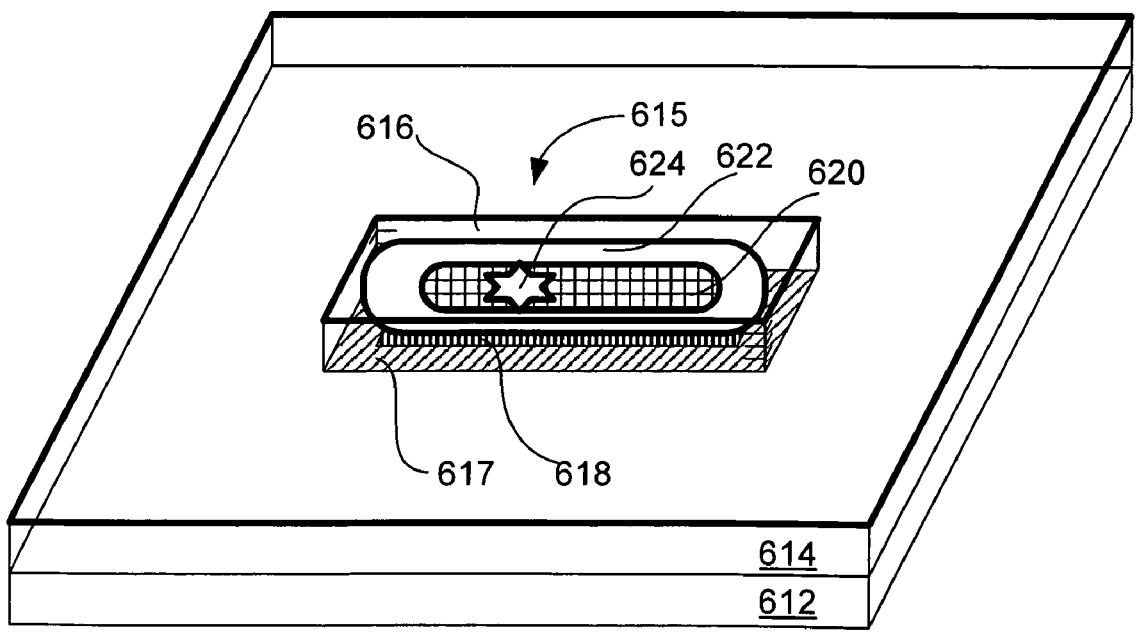

FIGS. 6A-6C and 7A-7C illustrate a method of placing a nanomoiety 620 at a deterministically located bind site 615 on a substrate 612 where it is desired for a length aspect of the nanomoiety 620 to be parallel to the surface 617 of the substrate 612. FIGS. 6A-6C are cross sectional views while FIGS. 7A-7B are dimetric three-dimensional views. Feature numbering is intended to be consistent among FIGS. 6A-6B and 7A-7C. The figures are not to scale. Feature sizes are consistent among FIGS. 6A-6B, and among FIGS. 7A-7C. No attempt is made to maintain consistent feature sizes between the two sets of figures FIGS. 6A-6B and FIGS. 7A-7C.

FIG. 7A illustrates a binding site 615 prepared on a substrate 612 at a deterministic location. The hole 616 through location and alignment layer 614 has a width aspect 710 and a length aspect 712. The binding patch 618 is disposed on the portion of the substrate surface 617 exposed at the bottom of the hole 616. In the embodiment shown, the binding patch 618 is of uniform composition, but it will be appreciated that a binding patch of varied composition can be used, for example, similar to binding patch 318 discussed above, comprising multiple sections such as section 318-1 and 318-2.

A delivery vehicle 622 illustrated in FIG. 6A is one of many such in a delivery medium 628 introduced to the binding site 615. The delivery vehicle has a diameter aspect 714 and a length aspect 716.

The delivery vehicle is associated with a nanomoiety 620 that can be useful, for example, as the channel element of a nanoscale transistor. The nanomoiety may be, for example, a single-walled carbon nanotube or a semiconductor nanowire. The nanomoiety has a length aspect and a diameter aspect.

A reporter entity 624 has utility like that of other reporter entities discussed herein. The reporter entity 624 is shown associated with the nanomoiety 620. In other embodiments the reporter entity 624 can be associated with the delivery vehicle 622.

The diameter of the diameter aspect of the nanomoiety 620 is a first characteristic dimension of the nanomoiety for the purposes of this disclosure. The width of the width aspect 710 of the hole 616 is a second characteristic dimension of the binding site 615 for the purposes of this disclosure. The diameter of the diameter aspect 714 of the delivery vehicle 622 is a third characteristic dimension of the delivery vehicle 622 for the purposes of this disclosure. For the embodiment illustrated the second characteristic dimension is larger than the first characteristic dimension, the third characteristic dimension is larger than the first characteristic dimension, and the third characteristic dimension is smaller than the second characteristic dimension.

A binding region 626 occupies a portion of the length aspect of the delivery vehicle 622. In the embodiment shown, the binding region 626 is placed on one side of the length aspect, but it may wrap around the length aspect in a cylindrical fashion, or be spit into rings of varying binding affinity properties, or varied in some other fashion, without departing from the spirit and scope of the present disclosure.

When the binding site 615 is exposed to the delivery medium 628, the delivery vehicle 622 by chance happens to be the one delivery vehicle that nestles into the hole 616, thereby precluding other delivery vehicles from nestling into the hole 616, and with the particular orientation enabling the binding region 626 to bind to the binding patch 618, thereby precluding any other delivery vehicle from binding to the binding patch 618.

FIG. 6B and FIG. 7B illustrate the delivery vehicle 622 bound in place at the binding site 615 after the delivery medium 628 has been removed and any unbound delivery vehicles have been washed away.

Figure 7C:
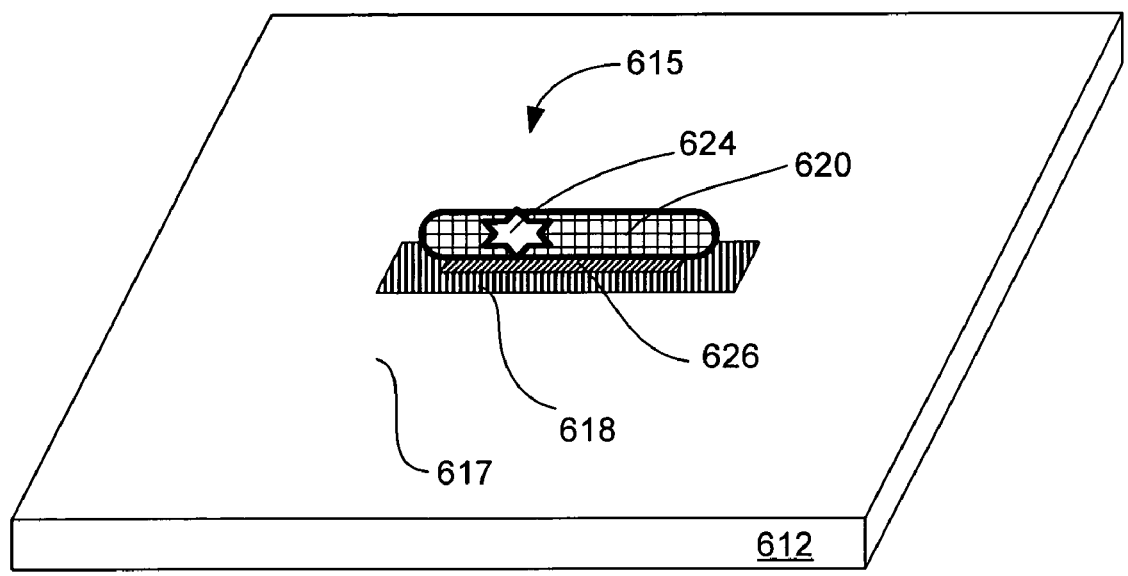

FIG. 6C and FIG. 7C illustrate the nanomoiety 620 retained in place at the binding site 615 after the location and alignment layer 614 has been removed and after the nanomoiety 620 has been rendered from the delivery vehicle 622. The nanomoiety 620 has a retention characteristic that keeps it bound in place after the rendering process. The removal of the location and alignment layer 614 advantageously removes any delivery vehicles that had been undesirably bound to the location and alignment layer.

The above descriptions of specific embodiments are not intended to be limiting, but instead are intended to illustrate a subset of the variety of possible embodiments within the spirit and scope of the present disclosure. For example, it will be appreciated that the use of complementary oligonucleotide pairs on binding regions and binding patches as described above herein can permit two or more different sets of complementary oligonucleotide pairs to be employed simultaneously.

Thus, for example, if it is desired to fabricate complementary MOS (CMOS) transistor circuits using p-type and n-type nanowires, one set of delivery vehicles associated with p-type nanowires can have a binding region decorated with oligonucleotides complementary to binding sites where p-type transistors are to be fabricated but that will not bond at the n-type sites, and a second set of set of delivery vehicles associated with n-type nanowires can have a binding region decorated with oligonucleotides complementary to binding sites where n-type transistors are to be fabricated but which will not bind at the p-type sites. Both types of delivery vehicles can be placed in one delivery medium without adhering to one another, and both types of nanosites can be prepared on one substrate. Thus both p-type and n-type nanowires can be placed at their respective nanosites simultaneously, facilitating the fabricating of CMOS circuits. In addition, more than two sets of different types of delivery vehicles can be delivered to more than two types of nanosites by expanding the set of pairs of complementary oligonucleotides used, and/or by employing other non-interacting sets of binding mechanisms, to achieve a variety of useful purposes.

From the description of particular instances herein it is evident that the methods of the present disclosure can be employed to provide deterministic location of nanomoieties, in sparse arrays, with particular orientations, with particular polarities, in multiple types, and to provide any or all combinations of these characteristics in a particular embodiment.

It will be appreciated that the use of methods that introduce some degree of randomness and/or jitter to the location of a binding site which would otherwise be deterministically placed falls within the spirit and scope of the present disclosure.

It should be emphasized that many variations and modifications may be made to the above-described embodiments. All such modifications and variations are intended to be included herein within the scope of this disclosure and protected by the following claims.

I claim the following:

1. A method of placing a nanomoiety at a deterministic location on a substrate, the method comprising:
   preparing a nanomoiety having a first characteristic dimension;
   providing a substrate having a surface;
   providing a nanoscale binding site at a deterministic location on the surface, the binding site having a binding patch, the binding site having a second characteristic dimension larger than the first characteristic dimension of the nanomoiety;
   associating the nanomoiety with a nanoscale delivery vehicle, the delivery vehicle having a third characteristic dimension larger than the first characteristic dimension of the nanomoiety, one of the nanoscale moiety and the nanoscale delivery vehicle having a binding region capable of binding at the binding patch;
   exposing the surface to a fluid delivery medium containing the nanomoiety associated with the delivery vehicle;
   stochastically contacting the binding region to the binding patch thereby binding the delivery vehicle to the substrate; and
   rendering the nanoscale moiety from the delivery vehicle to leave the nanoscale moiety attached to the substrate, the nanoscale moiety having a retention characteristic for continued attachment to the substrate after rendering.

2. The method of claim 1, wherein the second characteristic dimension of the binding site is larger than the third characteristic dimension of the delivery vehicle.

3. The method of claim 1, wherein the second characteristic dimension of the binding site is smaller than the third characteristic dimension of the delivery vehicle.

4. The method of claim 1, wherein a plurality of nanomoieties are present in the delivery medium, each nanomoiety being associated with a delivery vehicle.

5. The method of claim 1, wherein a plurality of nanoscale binding sites are present on the surface, wherein each binding site has a binding patch, wherein each binding site has the second characteristic dimension larger than the first characteristic dimension of the nanomoiety.

6. The method of claim 5, wherein each nanoscale binding site is prepared at a deterministic location.

7. The method of claim 1, further including preparing a location layer on the surface of the substrate, the location layer having a hole therein, wherein during the step of exposing of the surface to a fluid delivery medium containing the nanomoiety associated with the delivery vehicle, the hole in conjunction with the delivery vehicle provides a location function for the delivery vehicle at the binding site.

8. The method of claim 1, further including disposing a location and alignment layer on the surface of the substrate, the location and alignment layer having a hole therein, wherein during the step of exposing of the surface to a fluid delivery medium containing the nanomoiety associated with the delivery vehicle, the hole in conjunction with the delivery vehicle provides a location and alignment function for the delivery vehicle at the binding site.

9. The method of claim 1, further including providing a reporter entity associated with one of the delivery vehicle and the nanomoiety.

10. The method of claim 9, further including detecting the reporter entity after one of the step of stochastically binding and the step of rendering.

11. The method of claim 1, wherein a multiplicity of nanoscale sites is prepared on the surface of the substrate, wherein each site has the third characteristic dimension greater than the first characteristic dimension of the nanomoiety, each site having a binding patch exposed to a delivery medium containing a multiplicity of nanomoieties, wherein each nanomoiety is associated with one of a multiplicity of delivery vehicles.

12. The method of claim 11, wherein a plurality of reporter entities is present in the delivery medium, each reporter entity being associated with one of a nanomoiety and a delivery vehicle.

13. The method of claim 11, wherein the number of nanomoieties present in the delivery medium is greater than the number of nanoscale sites on the surface of the substrate.

14. The method of claim 11, further including washing the surface of the substrate to remove any unbound delivery vehicles after one of the step of stochastically binding and the step of rendering.

15. The method of claim 7, further including removing the location layer after one of the step of stochastically binding and the step of rendering.

16. The method of claim 8, further including removing the location and alignment layer after one of the step of stochastically binding and the step of rendering.

17. The method of claim 4, wherein the shape of each delivery vehicles precludes more than one binding region at a time from binding at the binding patch.

18. The method of claim 11, wherein the shape of each delivery vehicle precludes more than one binding region at a time from binding at each of the multiplicity of binding patches.

19. The method of claim 11, wherein the third characteristic dimension of each delivery vehicle is less than the second characteristic dimension of each binding site and greater than half of the second characteristic dimension of each binding site.

20. The method of claim 11, wherein the third characteristic dimension of each delivery vehicle is greater than twice the second characteristic dimension of each binding site.

21. The method of claim 1, wherein the binding patch includes a first nucleotide and the binding region includes a second nucleotide, wherein the first nucleotide and the second nucleotide are complementary.

22. The method of claim 21, further comprising a second nanomoiety that is associated with a second nanoscale delivery vehicle, wherein one of the second nanomoiety and the second nanoscale delivery vehicle has a second binding region, wherein the substrate has a second nanoscale binding site at a deterministic location on the surface of the substrate, the second binding site having a second binding patch, wherein the binding patch includes a third nucleotide and the binding region includes a fourth nucleotide, wherein the third nucleotide and the fourth nucleotide are complementary, and wherein each of the first nucleotide and the second nucleotide are not complementary for either of the third nucleotide and the fourth nucleotide.

23. The method of claim 1, wherein the nanoscale moiety is a seed particle.

24. The method of claim 23, further comprising:
   forming a mandrel on the seed particle;
   forming a plurality of layers on the substrate around the mandrel, wherein the layers alternate between an insulator layer and a conductor layer; and
   forming a nanohole with a diameter of the mandrel by removing the mandrel and the seed particle.

25. The method of claim 1, wherein the nanoscale moiety is a mandrel.

26. The method of claim 25, further comprising:
  forming a plurality of layers on the substrate around the mandrel, wherein the layers alternate between an insulator layer and a conductor layer; and
  forming a nanohole with a diameter of the mandrel by removing the mandrel.

* * * * *